US005698579A

United States Patent [19]
Muller

[11] Patent Number: 5,698,579
[45] Date of Patent: Dec. 16, 1997

[54] CYCLIC AMIDES

[75] Inventor: George W. Muller, Bridgewater, N.J.

[73] Assignee: Celgene Corporation, Warren, N.J.

[21] Appl. No.: 703,708

[22] Filed: Aug. 27, 1996

Related U.S. Application Data

[63] Continuation-in-part of Ser. No. 258,587, Jun. 10, 1994, Pat. No. 5,605,914, which is a continuation-in-part of Ser. No. 87,510, Jul. 2, 1993, abandoned, and Ser. No. 140,237, Oct. 20, 1993, Pat. No. 5,463,063.

[51] Int. Cl.$^6$ .......................... C07D 209/34; A61K 31/40
[52] U.S. Cl. .............................................. 514/416; 548/512
[58] Field of Search .............................. 548/512; 514/416

[56] References Cited
PUBLICATIONS

Chemical Abstracts #117:251172, 1992, by Padwa.
Chemical Abstracts #116:152338, 1992, Ocain.
Chemical Abstracts #115:256655, 1991, Ocain.
Chemical Abstracts #106:119777, Nefkens, 1985.

*Primary Examiner*—Alan L. Rotman
*Assistant Examiner*—D. Margaret M. Mach
*Attorney, Agent, or Firm*—Mathews, Collins, Shepherd & Gould, P.A.

[57] ABSTRACT

Cyclic amides are inhibitors of tumor necrosis factor and can be used to combat cachexia, endotoxic shock, and retrovirus replication. A typical embodiment is 3-phenyl-3-(1-oxoisoindolin-2-yl)propionamide.

35 Claims, No Drawings

CYCLIC AMIDES

CROSS REFERENCE TO RELATED APPLICATIONS

This is a continuation-in-part of Ser. No. 08/258,587 filed Jun. 10, 1994, now U.S. Pat. No. 5,605,914, which in turn is a continuation-in-part of Ser. No. 08/087,510 filed Jul. 2, 1993, now abandoned, and Ser. No. 08/140,237 filed Oct. 20, 1993, now U.S. Pat. No. 5,463,063, the disclosures of which are incorporated herein by reference.

BACKGROUND OF THE INVENTION

The present invention relates a method of reducing levels of TNFα in a mammal and to compounds and compositions useful therein. TNFα, or tumor necrosis factor α, is a cytokine which is released primarily by mononuclear phagocytes in response to various immunostimulators. When administered to animals or humans it causes inflammation, fever, cardiovascular effects, hemorrhage, coagulation, and acute phase responses similar to those seen during acute infections and shock states.

Excessive or unregulated TNFα production has been implicated in a number of disease conditions. These include endotoxemia and toxic shock syndrome {Tracey et al., Nature 330, 662–664 (1987) and Hinshaw et al., Circ. Shock 30,279–292 (1990)}; cachexia {Dezube et al., Lancet, 335 (8690), 662 (1990)} and Adult Respiratory Distress Syndrome where TNFα concentration in excess of 12,000 pg/mL have been detected in pulmonary aspirates from ARDS patients {Millar et al., Lancet 2(8665), 712–714 (1989)}. Systemic infusion of recombinant TNFα also resulted in changes typically seen in ARDS {Ferrai-Baliviera et al., Arch. Surg. 124(12), 1400–1405 (1989)}.

TNFα appears to be involved in bone resorption diseases, including arthritis where it has been determined that when activated, leukocytes will produce a bone-resorbing activity, and data suggest that TNFα contributes to this activity. {Bertolini et al., Nature 319, 516–518 (1986) and Johnson et al., Endocrinology 124(3), 1424–1427 (1989).}TNFα has been shown to stimulate bone resorption and inhibit bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {Calci. Tissue Int. (US) 46(Suppl.), S3–10 (1990)}. In Graff versus Host Reaction, increased serum TNFα levels have been associated with major complication following acute allogenic bone marrow transplants {Holler et al., Blood, 75(4), 1011∝1016 (1990)}.

Cerebral malaria is a lethal hyperacute neurological syndrome associated with high blood levels of TNFα. Levels of serum TNFα correlated directly with the severity of disease and the prognosis in patients with acute malaria attacks {Grau et al., N. Engl. J. Med. 320(24), 1586–1591 (1989)}.

TNFα plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344:245–247 (1990)}. High levels of TNFα production (in the serum and in isolated macrophages) have been demonstrated in animal models of silica and asbestos induced fibrosis {Bissonnette et al., Inflammation 13(3), 329–339 (1989)}. Alveolar macrophages from pulmonary sarcoidosis patients have also been found to spontaneously release massive quantities of TNFα as compared with macrophages from normal donors {Baughman et al., J. Lab. Clin. Med. 115(1), 36–42 (1990)}.

TNFα is implicated in the inflammatory response which follows reperfusion, called reperfusion injury, and is a major cause of tissue damage after loss of blood flow {Vedder et al., PNAS 87, 2643–2646 (1990)}. TNFα also alters the properties of endothelial cells and has various pro-coagulant activities, such as producing an increase in tissue factor pro-coagulant activity, suppression of the anticoagulant protein C pathway, and down-regulating the expression of thrombomodulin {Sherry et al., J. Cell Biol. 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J. Path. 135(1), 121–132(1989)}.

Moreover, it now is known that TNFα is a potent activator of retrovirus replication including activation of HIV-1. {Duh et al., Proc. Nat. Acad. Sci 86, 5974–5978 (1989); Poll et al., Proc. Nat. Acad. Sci. 87, 782–785 (1990); Monto et al., Blood 79, 2670 (1990); Clouse et al., J. Immunol. 142, 431–438 (1989); Poll et al., AIDS Res. Hum. Retrovirus, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocytes activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for vital replication and the level of viral replication is dependent upon the activation state of the cells. {Rosenberg et al., The Immunopathogenesis of HIV Infection, Advances in Immunology, 57 (1989)}. Cytokines, such as TNFα, have been shown to activate HIV replication in monocytes and/or macrophages {Poli et al. Proc. Natl. Acad. Sci., 87, 782–784 (1990)}, therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osborn, et al., PNAS 86 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., PNAS 86, 2365–2368 (1989)}. A molecular mechanism for the virus inducing activity is suggested by TNFα's ability to activate a gene regulatory protein NFκB found in the cytoplasm of cells, which promotes HIV replication through binding to a viral regulatory gene sequence (LTR) {Osborn et al., PNAS 86, 2336–2340 (1989)}. TNFα in AIDS associated cachexia is suggested by elevated serum TNFα and high levels of spontaneous TNFα production in peripheral blood monocytes from patients {Wright et al. J. Immunol. 141(1), 99–104 (1988)}. TNFα has been implicated in various roles with other viral infections, such as the cytomegalia virus (CMV), influenza virus, adenovirus, and the herpes family of viruses for similar reasons as those noted.

Reducing or inhibiting the production or action of TNFα, therefore, provides a potent therapeutic strategy for alleviation of many inflammatory, infectious, immunological or malignant conditions. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Efforts directed to the suppression of the effects of TNFα have ranged from the utilization of steroids such as dexamethasone and prednisolone to the use of both polyclonal and monoclonal antibodies {Beutler et al., Science 234, 470–474 (1985); WO 92/11383 }.

The nuclear factor κB (NFκB) is a pleiotropic transcriptional activator (Lenardo, et al. Cell 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al. J. Biol. Chem. 1993, 17762–66; Duh et al. Proc. Natl. Acad. Sci. 1989, 86, 5974–78; Bacheleric et al. Nature 1991, 350, 709–12; Boswas et al. J. Acquired Immune Deficiency Syndrome 1993, 6, 778–786; Suzuki et al. Biochem. And Biophys. Res. Comm. 1993, 193,277–83; Suzuki et al. Biochem. And Biophys. Res Comm. 1992, 189, 1709–15; Suzuki et al. Biochem. Mol. Bio. Int. 1993, 31(4), 693–700; Shakhov et al. Proc. Natl. Acad Sci. USA 1990, 171, 35–47; and Staal et al. Proc. Natl. Acad. Sci. USA 1990, 87, 9943–47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, intimation, and other conditions (Lowe and Cheng, Drugs of the Future, 17(9), 799–807, 1992). It has been shown that the elevation of cAMp in inflammatory leukocytes inhibits their activation and the subsequent release of inflammatory mediators including TNFα and NFκB. Increased levels of cAMP also leads to the relaxation of airway smooth muscle. The primary cellular mechanism for the inactivation of cAMP is the breakdown of cAMP by a family of isoenzymes referred to as cyclic nucleotide phosphodiesterases (PDE), of which seven are known. It is recognized, for example, that the inhibition of PDE type IV is particularly effective in both the inhibition of inflammatory mediator release and the relaxation of airway smooth muscle. Thus, compounds which inhibit PDE IV exhibit the desirable inhibition of inflammation and relaxation of airway smooth muscle with a minimum of unwanted side effects, such as cardio-vascular or anti-platelet effects. It is now known that inhibition of TNFα production can be a consequence of inhibition of PDE IV. L. J. Lombardo, Current Pharmaceutical design, 1,255–268 (1995).

DETAILED DESCRIPTION

The present invention is based on the discovery that a class of non-polypeptide amides more fully described herein appear to inhibit the action of TNFα and to elevate cAMP levels.

A first aspect of the present invention pertains to compounds of the formula:

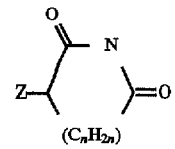

in which Z is:

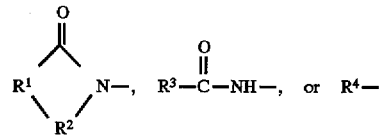

$R^1$ is the divalent residue of (i) 3,4-pyridine, (ii) pyrrolidine, (iii) imidizole, (iv) naphthalene, (v) thiophene, or (vi) a straight or branched alkane of 2 to 6 carbon atoms, unsubstituted or substituted with phenyl or phenyl substituted with nitro, cyano, trifluoromethyl, carbethoxy, carbomethoxy, carbopropoxy, acetyl, carbamyl, acetoxy, carboxy, hydroxy, amino, alkyl of 1 to 10 carbon atoms, alkoxy of 1 to 10 carbon atoms, or halo, wherein the divalent bonds of said residue are on vicinal ring carbon atoms;

R2 is —CO— or —SO2—;

$R^3$ is (i) phenyl substituted with 1 to 3 substituents each selected independently from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (ii) pyridyl, (iii) pyrrolyl, (iv) imidazolyl, (v)naphthyl, (vi) thienyl, (vii) quinolyl, (viii) furyl, or (ix) indolyl;

$R^4$ is alanyl, arginyl, glycyl, phenylglycyl, histidyl, leucyl, isoleucyl, lysyl, methionyl, propyl, sarcosyl, seryl, homoseryl, threonyl, thyronyl, tyrosyl, valyl, benzimidol-2-yl, benzoxazol-2-yl, phenylsulfonyl, methylphenylsulfonyl, or phenylcarbamoyl; and n has a value of 1, 2, or 3.

More particularly, a first preferred subclass pertains to compounds of the formula:

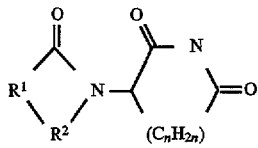
IA.

in which $R^1$ is the divalent residue of (i) 3,4-pyridine, (ii) pyrrolidine, (iii) imidizole, (iv) naphthalene, (v) thiophene, or (vi) a straight or branched alkane of 2 to 6 carbon atoms, unsubstituted or substituted with phenyl or phenyl substituted with nitro, cyano, trifluoromethyl, carbethoxy, carbomethoxy, carbopropoxy, acetyl, carbamyl, acetoxy, carboxy, hydroxy, amino, alkyl of 1 to 10 carbon atoms, alkoxy of 1 to 10 carbon atoms, or halo, wherein the divalent bonds of said residue are on vicinal ring carbon atoms; $R^2$ is —CO— or —SO$_2$—; and n has a value of 1, 2, or 3.

Preferred compounds of Formula IA include those in which $R^1$ is a divalent residue of pyridine, naphthalene or imidazole, $R^2$ is —CO—, and n is 2.

A second preferred subclass pertains to compounds of the formula:

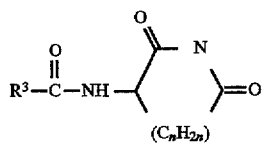
IB.

in which $R^3$ is (i) phenyl substituted with nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (ii) pyridyl, (iii) pyrrolyl, (iv) imidazolyl, (v) naphthyl, (vi) thienyl, (vii) quinolyl, (viii) furyl, or (ix) indolyl; and n has a value of 1, 2, or 3.

Preferred compounds of Formula IB are those wherein $R^3$ is trifluoromethylphenyl, cyanophenyl, methoxyphenyl, fluorophenyl, or furyl, and n is 2.

A third preferred subclass pertains to compounds of the formula:

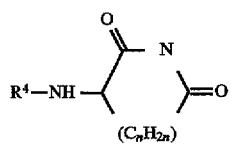
IC.

in which $R^4$ is alanyl, arginyl, glycyl, phenylglycyl, histidyl, leucyl, isoleucyl, lysyl, methionyl, propyl, sarcosyl, seryl, homoseryl, threonyl, thyronyl, tyrosyl, valyl, benzimidol-2-yl, benzoxazol-2-yl, phenylsulfonyl, methylphenylsulfonyl, or phenylcarbamoyl, and n has a value of 1, 2, or 3.

Preferred compounds of Formula IC are those wherein $R^4$ is phenylsulfonyl or 2-amino-3-phenylpropanoyl and n is 2.

A second aspect of the present invention pertains to compounds of the formula:

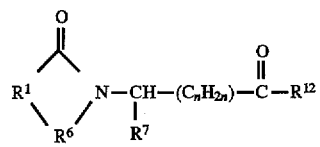
II.

in which $R^5$ is (i) o-phenylene, unsubstituted or substituted with 1 to 4 substituents each selected independently from nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, or halo, or (ii) the divalent residue of pyridine, pyrrolidine, imidizole, naphthalene, or thiophene, wherein the divalent bonds are on vicinal ring carbon atoms;

$R^6$ is —CO—, —CH$_2$—, or —SO$_2$—;

$R^7$ is (i) hydrogen if $R^6$ is —SO$_2$—, (ii) straight, branched, or cyclic alkyl of 1 to 12 carbon atoms, (iii) pyridyl, (iv) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (v) alkyl of 1 to 10 carbon atoms, (vi) benzyl unsubstituted or substituted with 1 to 3 substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (vii) naphthyl, (viii) benzyloxy, or (ix) imidazol-4-ylmethyl;

$R^{12}$ is —OH, alkoxy of 1 to 12 carbon atoms, or

n has a value of 0, 1, 2, or 3;

$R^{8'}$ is hydrogen or alkyl of 1 to 10 carbon atoms; and $R^{9'}$ is hydrogen, alkyl of 1 to 10 carbon atoms, —COR$^{10}$, or —SO$_2$R$^{10}$ in which $R^{10}$ is hydrogen, alkyl of 1 to 10 carbon atoms, or phenyl.

A first preferred subclass of Formula II pertains to compounds of the formula

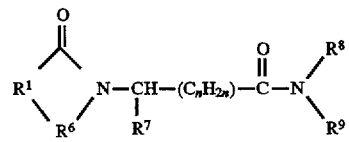
IIA.

in which $R^5$ is (i) o-phenylene, unsubstituted or substituted with 1 to 4 substituents each selected independently from nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, or halo, or (ii) the divalent residue of pyridine, pyrrolidine, imidizole, naphthalene, or thiophene, wherein the divalent bonds are on vicinal ring carbon atoms;

R6 is —CO—, —CH2—, or —SO2—;

$R^7$ is (i) hydrogen if $R^6$ is —SO$_2$—, (ii) straight, branched, or cyclic alkyl of 1 to 12 carbon atoms, (iii)

pyridyl, (iv) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (v) alkyl of 1 to 10 carbon atoms, (vi) benzyl unsubstituted or substituted with 1 to 3 substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (vii) naphthyl, (viii) benzyloxy, or (ix) imidazol-4-ylmethyl;

n has a value of 0, 1, 2, or 3; $R^8$ is hydrogen or alkyl of 1 to 10 carbon atoms; and $R^9$ is hydrogen, alkyl of 1 to 10 carbon atoms, —$COR^{10}$, or —$SO_2R^{10}$ in which $R^{10}$ is hydrogen, alkyl of 1 to 10 carbon atoms, or phenyl.

Preferred compounds of Formula IIA are those in which $R^5$ is o-phenylene, $R^6$ is —CO—; $R^7$ is phenyl, substituted phenyl or pyridyl; n is 0 or 1, and each of $R^8$ and $R^9$ is hydrogen.

A second preferred subclass of Formula II pertains to compounds of the formula:

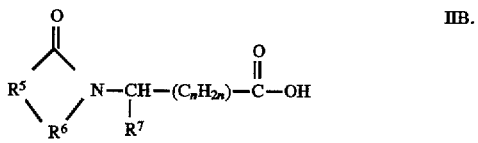

IIB.

in which $R^5$ is (i) o-phenylene, unsubstituted or substituted with 1 to 4 substituents each selected independently from vitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, alkoxy of 1 to 10 carbon atoms, or halo, or (ii) the divalent residue of pyridine, pyrrolidine, imidizole, naphthalene, or thiophene, wherein the divalent bonds are on vicinal ring carbon atoms;

$R^6$ is —CO—, —$CH_2$—, or —$SO_2$—;

$R^7$ is (i) hydrogen if $R^6$ is —$SO_2$—, (ii) straight, branched, or cyclic alkyl of 1 to 12 carbon atoms, (iii) pyridyl, (iv) phenyl or phenyl substituted with one or more substituents each selected independently of the other from vitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (v) alkyl of 1 to 10 carbon atoms, (vi) benzyl unsubstituted or substituted with 1 to 3 substituents selected from the group consisting of vitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (vii) naphthyl, (viii) benzyloxy, or (ix) imidazol-4-ylmethyl; and n has a value of 0, 1, 2, or 3.

Preferred compounds of Formula IIB are those in which $R^5$ is o-phenylene, $R^6$ is —CO—; $R^7$ is phenyl, substituted phenyl or pyridyl; and n is 0 or 1.

A third preferred subclass of Formula II pertains to compounds of the formula:

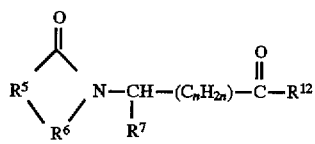

IIC.

in which $R^5$ is (i) o-phenylene, unsubstituted or substituted with 1 to 4 substituents each selected independently from nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, alkoxy of 1 to 10 carbon atoms, or halo, or (ii) the divalent residue of pyridine, pyrrolidine, imidizole, naphthalene, or thiophene, wherein the divalent bonds are on vicinal ring carbon atoms;

$R^6$ is —CO—, —$CH_2$—, or —$SO_2$—;

$R^7$ is (i) hydrogen if $R^6$ is —$SO_2$—, (ii) straight, branched, or cyclic alkyl of 1 to 12 carbon atoms, (iii) pyridyl, (iv) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (v) alkyl of 1 to 10 carbon atoms, (vi) benzyl unsubstituted or substituted with 1 to 3 substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (vii) naphthyl, (viii) benzyloxy, or (ix) imidazol-4-ylmethyl;

R12 is —OH or alkoxy of 1 to 12 carbon atoms; and n has a value of 0, 1, 2, or 3.

Preferred compounds of Formula IIC are those in which $R^5$ is o-phenylene, particularly aminophenylene, $R^6$ is —CO—; $R^7$ is phenyl, substituted phenyl, particularly alkoxyphenyl and dialkoxyphenyl, or pyridyl; and n is 0 or 1.

The present invention also pertains to the physiologically acceptable non-toxic acid addition salts of the compounds of Formula I. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Typical compounds of this invention include 2-(2,6-dioxo-3-piperidinyl)-4-azaisoindoline-1,3-dione; 2-(2,6-dioxo-3-piperidinyl)-benzo[e]isoindoline-1,3-dione; 5-(2,6-dioxo-3-piperidinyl)-pyrrolo[3,4-d]imidazole-4,6-dione; 3-(trifluoromethylphenylcarboxamido)piperidine-2,6-dione; 3-(cyanophenylcarboxamido)piperidine-2,6-dione; 3-(methoxyphenylcarboxamido)-piperidine-2,6-dione; 3-(3-pyridylcarboxamido)piperidine-2,6-dione; 3-(2-furylcarboxamido)piperidine-2,6-dione; 3-phenylsulfonamidopiperidine-2,6-dione; 3-(2-amino-3-phenylpropanamido)-piperidine-2,6-dione; α-phthalimidophenylacetamide; 3-phthalimido-3-phenylpropionamide; 2-phthalimido-3-phenylpropionamide; 2-phthalimido-3-(4-hydroxyphenyl) propionamide; 3-phthalimido-3-phenylpropionic acid; α-phthalimido4-hydroxyphenylacetic acid; α-phthalimidophenylacetic acid; α-phthalimido-4- fluorophenylacetic acid; α-phthalimido-2-fluorophenylacetic acid; α-phthalimido-4-fluoro-phenyl) acetamide; 2-phthalimido-3-phenylpropionic acid; 2-phthalimido-4-methylpentanoic acid; 3-phenylcarboxamidopiperidine-2,6-dione; α-phthalimidoacetamide; 3-phthalimidopropionamide; 3-phthalimidoimidazoline-2,5-dione; 3-phenylcarboxamidopropionamide; 2-phthalimido-3-carbamoylpropionic acid; 2-(1,3-dioxo-4-azaisoindolin-2-yl)-3-carbamoylpropionic acid; 3-(1,3-dioxo-4-azaisoindolin-2-yl)piperidine-2,6-dione; 1,3-dioxo-4-azaisoindolin-2-ylacetamide; 3-phthalimido-3-carbamoylpropionic acid; 4-phthalimidobutyramide; 4-phthalimidobutyric acid; methyl 3-phthalimido-3-(4-methoxyphenyl)propionate; ethyl 3-phthalimido-3-(4-methoxyphenyl)propionate; methyl 3-phthalimido-3-phenylpropionate; and propyl 3-phthalimido-3-(4-methoxyphenyl)propionate; α-(1-oxoisoindolin-2-yl) phenylacetic acid; α-(1-oxoisoindolin-2-yl) phenylacetamide; 3-phenyl-2-(1-oxoisoindolin-2-yl) propionic acid; 3-phenyl-2-(1-oxoisoindolin-2-yl) propionamide; 3-phenyl-3-(1-oxoisoindolin-2-yl)propionic acid; 3-phenyl-3-(1-oxoisoindolin-2-yl)propionamide; 3-(4-methoxyphenyl)-3-(1-oxoisoindolin-2-yl)propionic acid; 3-(4-methoxyphenyl)3-(1-oxoisoindolin-2-yl) propionamide; 3-(3,4-dimethoxyphenyl)-3-(1-oxoisoindolin-2-yl)propionic acid; 3-(3,4-dimethoxyphenyl)-3-(1-oxoisoindolin-2-yl)propionamide; 3-(3,4-diethoxyphenyl)-3-(1-oxoisoindolin-2-yl)propionic acid; 3-(3,4-diethoxyphenyl)-3-phthalimidopropionamide; 3-phthalimido-3-(4-propoxyphenyl)propionic acid; 3-phthalimido-3-(4-propoxyphenyl)propionamide; ethyl 3-amino-3-(3-pyridyl)propionate hydrochloride; ethyl 3-phthalimido-3-(3-pyridyl)propionate; 3-phthalimido-3-(3,4-dimethoxyphenyl)propionic acid; 3-phthalimido-3-(3,4-dimethoxyphenyl)propionamide; 3-phthalimido-3-(3-ethoxy-4-methoxyphenyl)propionamide; ethyl 3-amino-3-(3,4-dimethoxyphenyl)propionate; ethyl 3-phthalimido-3-(3,4-dimethoxyphenyl)propionate; N-amyl 3-phthalimido-3-(3,4-dimethoxyphenyl)propionamide; N-benzyl 3-phthalimido-3-(3,4-dimethoxyphenyl)propionamide; N-ethyl 3-phthalimido-3-(3,4-dimethoxyphenyl) propionamide; 3-phthalimido-3-(4-ethoxyphenyl)propionic acid; 3-phthalimido-3-(4-ethoxyphenyl)propionamide; 3-(cis-hexahydrophthalimido)-3-phenylpropionic acid; 3-(cis-hexahydrophthalimido)-3-phenylpropionamide; 3-(4-methylphthalimido)-3-phenylpropionamide; 3-(cis-5-norbonene-endo-2,3-dicarboxylic imide)-3-phenylpropionic acid; 3-(2,3,4,5-tetrachlorophthalimido)-3-(4-methoxyphenyl)propionic acid; 3-(2,3,4,5-tetrafluorophthalimido)-3-(4-methoxyphenyl)propionic acid; 3-(1-oxo-4,5,6,7-tetrafluoroisoindolin-2-yl)-3-(3-ethoxy-4-methoxyphenyl)propionic acid; 3-(1-oxo-4,5,6,7-tetrafluoroisoindolin-2-yl)-3-(3-ethoxy-4-methoxyphenyl) propionamide; methyl 3-(1-oxo-4,5,6,7-tetrafluoroisoindolin-2-yl)-3-(3-ethoxy-4-methoxyphenyl) propionate; 3-(1-oxo-4,5,6,7-tetrafluoroisoindolin-2-yl)-3-(4-methoxyphenyl)propionic acid; 3-(1-oxo-4,5,6,7-tetrafluoroisoindolin-2-yl)-3-(4-methoxyphenyl) propionamide; methyl 3-(1-oxo-4,5,6,7-tetrafluoroisoindolin-2-yl)-3-(4-methoxyphenyl)propionate; 3-(1-oxo-4-aminoisoindolin-2-yl)-3-(4-methoxyphenyl) propionic acid; 3-(1-oxo-4-aminoisoindolin-2-yl)-3-(4-methoxyphenyl)propionamide; methyl 3-(1-oxo-4-aminoisoindolin-2-yl)-3-(4-methoxyphenyl)propionate; 3-(4-nitrophthalimido)-3-(4-methoxyphenyl)propionic acid; 3-phthalimido-3-(2-naphthyl)propionic acid; 3-phthalimido-3-(2-naphthyl)propionamide; methyl 3-(1,3-dioxo-5-azaisoindol-2-yl)-3-(3,4-dimethoxyphenyl)-propionate; 3-phthalimido-3-(4-benzyloxy-3-methoxyphenyl)propionic acid; 3-phthalimido-3-(4-benzyloxy-3-methoxyphenyl)propionamide; 3-phthalimido-3-(4-butoxy-3-methoxyphenyl)propionic acid; 3-phthalimido-3-(4-butoxy-3-methoxyphenyl) propionamide; α-(3,4,5,6-tetrachlorophthalimido) phenylacetic acid; α-(4,5-dichlorophthalimido)phenylacetic acid; α-(3-nitrophthalimido) phenylacetic acid; 3-(4-methoxyphenyl)-3-(3-nitrophthalimido)propionic acid; 3-(4,5-dichlorophthalimido)-3-(4-methoxyphenyl)propionic acid; 3-pyridinemethyl 3-phthalimido-3-(3,4-dimethoxyphenyl)propionate; N-3-methylpyridyl 3-phthalimido-3-(3,4-dimethoxyphenyl)propionamide; 3-phthalimido-3-(3,4-dichlorophenyl)propionamide; methyl 3-amino-3-(3,4-dimethoxyphenyl)propionate hydrochloride; methyl 3-phthalimido-3-(3,4-dimethoxyphenyl) propionate; methyl (S)-N-benzyl-N-(R)-α-methylbenzyl-3-(3,4-dimethoxyphenyl)propionate; methyl (S)-3-amino-3-(3,4-dimethoxyphenyl)propionate hydrochloride; methyl (S)-3-phthalimido-3-(3,4-dimethoxyphenyl)propionate; methyl (R)-3-(N-benzyl-N-(S)-α-methylbenzyl-amino)-3-(3,4-dimethoxyphenyl)propionate; methyl (R)-3-amino-3-(3,4-dimethoxyphenyl)propionate hydrochloride; 3-(1-oxoisoindolin-2-yl)-3-(3-propoxy-4-methoxyphenyl) propionic acid, 3-(1-oxoisoindolin-2-yl)-3-(3-butoxy-4-methoxyphenyl)propionic acid, 3-(1-oxoisoindolin-2-yl)-3-(3-propoxy-4-methoxyphenyl)propionamide, 3-(1-oxoisoindolin-2-yl)-3-(3-butoxy-4-methoxyphenyl) propionamide, methyl 3-(1-oxoisoindolin-2-yl)-3-(3-butoxy-4-methoxyphenyl)propionate, methyl 3-(1-oxoisoindolin-2-yl)-3-(3-propoxy-4-methoxyphenyl) propionate, and methyl (3R)-3-phthalimido-3-(3,4-dimethoxyphenyl)propionate.

The term alkyl as used herein denotes a univalent saturated branched or straight hydrocarbon chain. Unless otherwise stated, such chains can contain from 1 to 10 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, and the like. When qualified by "lower", the alkyl group will contain from 1 to 6 carbon atoms. The same carbon content applies to the parent term "alkane" and to derivative terms such as "alkoxy".

The compounds can be used, under the supervision of qualified professionals, to reduce the undesirable effects of TNFα. The compounds can be administered orally, rectally, or parenterally, alone or in combination with other therapeutic agents including antibiotics, steroids, etc., to a mammal in need of treatment. Oral dosage forms include tablets capsules, dragees, and similar shaped, compressed pharmaceutical forms. Isotonic saline solutions containing 20–100 mg/mL can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 10 to about 500 mg/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is observed following the initial treatment regimen, then the amount of compound administered can be increased by, for example, fifty percent a week.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus caprine arthritis virus, visna virus, and maedi virus, as well as other lentiviruses.

Certain of these compounds possess centers of chirality and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

The compounds can be prepared using methods which are known in general for the preparation of amides. An N-alkoxycarbonylimide and an amine thus are allowed to react in the presence of a base such as sodium carbonate or sodium bicarbonate substantially as described by Shealy et al., *Chem. & Ind.*, (1965) 1030–1031) and Shealy et al., *J. Pharm. Sci.* 57, 757–764 (1968) to yield the N-substituted amide. Alternatively, a cyclic acid anhydride can be reacted with an appropriate amine to form an amide. Formation of a cyclic amide also can be accomplished by refluxing a solution of an appropriately substituted dicarboxylic acid monoamide in anhydrous tetrahydrofuran with N,N'-carbonyldiimidazole In contrast to prior art methods which produced a yield of less than 50%, this reaction produces yields in excess of 60%, in some cases greater than 90%.

Prevention or inhibition of production of TNFα by these compounds can be conveniently assayed using anti-TNFα antibodies. For example, plates (Nunc Immunoplates, Roskilde, DK) are treated with 5 µg/mL of purified rabbit anti-TNFα antibodies at 4° C. for 12 to 14 hours. The plates then are blocked for 2 hours at 25° C. with PBS/0.05% Tween containing 5 mg/mL BSA. After washing, 100 µL of unknowns as well as controls are applied and the plates incubated at 4° C. for 12 to 14 hours. The plates are washed and assayed with a conjugate of peroxidase (horseradish) and mouse anti-TNFα monoclonal antibodies, and the color developed with o-phenylenediamine in phosphate-citrate buffer containing 0.012% hydrogen peroxide and read at 492 nm.

The following examples will serve to further typify the nature of this invention but should not be construed as a limitation in the scope thereof, which scope is defined solely by the appended claims.

EXAMPLE 1

A stirred suspension of (S)-glutamine (14.6 g, 100 mmol) and 2,3-pyridinedicarboxylic anhydride (14.9 g, 100 mmol) in 100 mL of acetic acid is heated and refluxed for 1 hour. The reaction solution is cooled to form a solid. The solid is removed by filtration and washed with acetic acid to yield 7.11 g (26%) of 2-(1,3-dioxo-4-azaisoindolin-2-yl) glutaramic acid. The product can be further purified by slurring in 700 mL of refluxing ethanol, cooling, filtering, and drying to produce a white powder with a melting point of 222°–226° C.; $^1$H NMR (DMSO-d$_6$) δ13.25 (br s, 1H, COOH), 9.04 (dd, 1H, J=1.2, 4.9 Hz, pyr), 8.37 (dd, 1H, J=1.2, 7.8 Hz, pyr), 7.85 (dd, 1H, J=4.9, 7.8 Hz, pyr), 7.20 (s 1_H, CONH$_2$), 6.73 (s, 1H, CONH$_2$), 4.83 (dd, 1H, J=10.2, 4.8 Hz, CHN), 2.55–1.90 (m, 4H, CH$_2$CH$_2$); $^{13}$C NMR (DMSO-d$_6$) δ1173.22, 170.21, 165.8, 165.7, 155.4, 150.9, 131.7, 128.3, 126.9, 51.5, 31.4, 24.0.

Utilization of asparagine in place of glutamine produces 2-(1,3-dioxo-4-azaisoindolin-2-yl)-malonamic acid.

By substituting equivalent amounts of 2,3-naphthalenedicarboxylic anhydride and 4,5-imidazoledicarboxylic anhydride for 2,3-pyridinedicarboxylic anhydride in the foregoing procedure, there are respectively obtained 2-(1,3-dioxobenzo[e] isoindolin-2-yl)glutaramic acid and 2-(4,6-dioxopyrrolo[3,4-d]imidazol-5-yl)glutaramic acid.

EXAMPLE 2

A stirred suspension of 1.39 g, 5.01 mmol, of 2-(1,3-dioxo-4-azaisoindolin-2-yl)gluaramic acid (see Example 1), N,N'-carbonyldiimidazole (0.890 g, 5.49 mmoL) and N,N-dimethylaminopyridine (0.005 g, 0.04 mmoL) in 20 mL of tetrahydrofuran is refluxed for 15 hours. The reaction slurry is cooled and the solid removed by filtration and washed with minimal tetrahydrofuran. 2-(2,6-Dioxo-3-piperidinyl)-4azaisoindoline-1,3-dione (0.859 g, 66%) is recovered as a white powder. $^1$H NMR (DMSO-d$_6$) δ11.18 (s, 1H, NHCO), 9.04 (d, 1H, J=5.0 Hz, pyr), 8.39 (d, 1H, J=7.7 Hz, pyr), 7.86 (dd, 1H, J=5.0, 7.7 Hz, pyr), 5.25 (dd, 1H, J=15.3, 13 Hz, 1H, CHCO), 3.05–2.75 (m, 1H, CH$_2$CO), 2.75 (m, 2H, CH$_2$CO, CH$_2$), 2.20–2.00 (m, 1H, CH$_2$CO, CH$_2$); $^{13}$C NMR (DMSO-d$_6$) δ172.6, 169.6, 165.4, 155.3, 150.8, 131.7, 128.2, 126.9, 49.0, 30.8, 21.8. Anal. Calcd for $C_{12}H_9N_3O_4$. Theory 55.60, 3.50, 16.21. Found 55.50, 3.53, 16.11.

Substitution of 2-(1,3-dioxo-4-azaisoindolin-2-yl) malonamic acid in the foregoing procedure yields 2-(2,5-dioxo-3-pyrrolidinyl)-4-azaisoindoline-1,3-dione.

By substituting equivalent amounts of 2-(1,3-dioxobenzo [e]isoindolin-2-yl)glutaramic acid and 2-(4,6-dioxopyrrolo [3,4-d]imidazol-5-yl)glutaramic acid in the foregoing procedure, there are respectively obtained 2-(2,6-dioxo-3-piperidinyl)-benzo[e]isoindoline-1,3-dione and 5-(2,6-dioxo-3-piperidinyl)-pyrrolo[3,4-d]imidazole-4,6-dione.

EXAMPLE 3

A solution of L-glutamine (2.92 g, 20.0 mmoL) and sodium hydroxide (20 mmoL) in water is added to a stirred solution of phenylisocyanate (2.4 g, 2.2 mL, 20 mmoL) in acetonitrile (40 mL). The reaction mixture is stirred for 45 hours and is partially concentrated to remove acetonitrile.

The reaction mixture is washed with ethyl acetate (2×25 mL each). The pH of the reaction mixture is adjusted to 1–2 with 4N hydrochloric acid. The slurry of the reaction mixture is filtered and the solid washed and dried to yield 4.70 g of N-phenyl-N'-(4-carboxybutyramide)urea (89%) as a white powder.

By substituting 4-trifluoromethylphenylisocyanate, 3-cyanophenylisocyanate, 2-methoxyphenylisocyanate, fur-2-ylisocyanate, and pyrid-3-ylisocyanate for phenylisocyanate in the foregoing procedure, there are respectively obtained N-(4-trifluoromethylphenyl)-N'-(4-carboxybutyramide)urea, N-(3-cyanophenyl)-N'-(4-carboxybutyramide)urea, N-(2-methoxyphenyl)-N'-(4-carboxybutyramide)urea, N-(fur-2-yl)-N'-(4-carboxybutyramide)urea, and N-(pyrid-3-yl)-N'(4-carboxybutyramide)urea.

EXAMPLE 4

N-Phenyl-N'-(4-carboxybutyramide)urea (2.00 g, 7.54 mmoL) is mixed with carbonyldiimidazole (1.24 g, 7.95 mmoL) in tetrahydrofuran (30 mL) is heated and refluxed for 16 hours. The reaction mixture is concentrated and the residue slurried in water (25 mL). The resulting slurry is filtered and the solid is washed with water and air dried to yield 0.63 g of 3-phenylcarboxamidopiperidine-2,6-dione which can be alternatively named as N-phenyl-N'-(2-glutarimide)urea as a white flocculent powder. After being allowed to stand, the filtrate is refiltered to yield 0.70 g of additional material. $^1$H NMR (DMSO-d$_6$) $\delta$8.51 (s, 1H, CONHCO), 7.6–7.2 (m, 6H, Ar, ArNH), 6.83 (s, 1H, N HCH), 4.26 (t, 1_H, CHCO), 2.4–1.8 (m, 4H, CH$_2$CH$_2$); $^{13}$C NMR (DMSO-d$_6$) $\delta$173.2, 155.6, 132.2, 128.7, 127.7, 126.7, 55.7, 29.8, 27.2. Anal. Calcd for C$_{12}$H$_{13}$N$_3$O$_3$. Theoretical: C, 58.29; H, 5.29; N, 16.99. Found: C, 58.12; H, 5.17; N, 17.02.

By substituting N-(4-trifluoromethylphenyl)-N'-(4-carboxybutyramide)urea, N-(3-cyanophenyl)-N'-(4-carboxybutyramide)urea, N-(2-methoxyphenyl)-N'-(4-carboxybutyramide)urea, N-(fur-2-yl)-N'-(4-carboxybutyramide)urea, and N-(pyrid-3-yl)-N'-(4-carboxybutyramide)urea for N-phenyl-N'-(4-carboxybutyramide)urea in the foregoing procedure there are respectively obtained 3-(4-trifluoromethylphenylcarboxamido)piperidine-2,6-dione, 3-(3-cyanophenylcarboxamido)piperidine-2,6-dione, 3-(2-methoxyphenyl-carboxamido)piperidine-2,6-dione, 3-(fur-2-ylcarboxamido)piperidine-2,6-dione, and 3-(pyrid-3-ylcarboxamido)piperidine-2,6-dione.

EXAMPLE 5

To a stirred mixture of phenylglycine (3.0 g, 20 mmoL) and sodium carbonate (2.23 g, 21 mmoL) in 450 mL of water is added N-carbethoxyphthalimide (4.38 g, 20 mmoL). After 45 minutes, the reaction slurry is filtered. The filtrate is stirred and the pH adjusted to 1–2 with 4N hydrochloric acid. After 1 hour, the resulting slurry is filtered and the solid washed with water. The solid is dried in vacuo (60° C., <1 mm) to afford 2.88 g (51%) of $\alpha$-phthalimidophenylacetic acid, which can be alternatively named as N-phthaloylphenylglycine, as a white powder.

Use of $\beta$-phenyl-$\beta$-alanine, $\alpha$-phenyl-$\beta$-alanine, histidine, and tyrosine in place of phenylglycine in the procedure of this example yields respectively 3-phthalimido-3-phenylpropionic acid, 3-phthalimido-2-phenylpropionic acid, 2-phthalimido-3-imidazolylpropionic acid, and 2-phthalimido-3-(4-hydroxyphenyl)propionic acid.

EXAMPLE 6

To a stirred mixture of $\alpha$-phthalimidophenylacetic acid (2.50 g, 8.89 mmoL) in tetrahydrofuran (50 mL) is added carbonyldiimidazole (1.50 g, 9.25 mmoL) and a few crystals of 4-dimethylaminopyridine. The reaction is then heated to 50° C. for 45 minutes. After the reaction mixture cools to room temperature, 1 mL of concentrated ammonium hydroxide is added via syringe. The reaction is stirred for 1 hour, then diluted with 50 mL of water and partially concentrated to remove the majority of the tetrahydrofuran. The resulting slurry is filtered and the solid washed with copious amounts of water. The solid is dried in vacuo (60° C., <1 mm) to afford 1.9 g (76%) of $\alpha$-phthalimidophenylacetamide, which may be alternatively named as N-phthaloylphenylglycinamide, as an off-white powder: mp 218°–220° C.; $^1$H NMR (DMSO-d$_6$) $\delta$9.00–7.75 (m, 4H, Ar), 7.61 (br s, 1H, CONH$_2$), 7.55–7.20 (m, 6H, Ar, CONH$_2$), 5.82 (s, 1H, CHCO$_2$); $^{13}$C NMR (DMSO-d$_6$) $\delta$168.2, 167.1, 135.6, 134.5, 131.4, 129.4, 127.9, 127.7, 123.1, 56.3. Anal (C$_{16}$H$_{12}$N$_2$O$_3$), C, H, N.

Use of 3-phthalimido-3-phenylpropionic acid, 2-phthalimido-3-phenylpropionic acid, 2-phthalimido-3-imidazolylpropionic acid, and 2-phthalimido-3-(4-hydroxyphenyl)propionic acid in place of $\alpha$-phthalimidophenylacetic acid in the procedure of this example yields respectively 3-phthalimido-3-phenylpropionamide, 2-phthalimido-3-phenylpropionamide, 2-phthalimido-3-imidazolylpropionamide, and 2-phthalimido-3-(4-hydroxy) phenylpropionamide.

EXAMPLE 7

To a stirred mixture of $\beta$-alanine (4.45 g, 50.0 mmoL) and sodium carbonate (5.35 g, 50.5 mmoL) in 100 mL of water is added N-carbethoxyphthalimide (10.95 g, 50.0 mmoL). After 1.5 hour, the reaction slurry is filtered. The filtrate is stirred and the pH adjusted to 1–2 with 4N hydrochloric acid. After 15 minutes, the resulting slurry is filtered and the solid washed with water. The solid is dried in vacuo (60° C., <1 mm) to afford 6.96 g (64%) of N-phthaloyl-$\beta$-alanine, which can be alternatively named as 3-phthalimidopropionic acid, as a white powder.

EXAMPLE 8

To a stirred solution of N-phthaloyl-$\beta$-alanine (2.19 g, 10.0 mmoL) in tetrahydrofuran (25 mL) is added carbonyl-diimidazole (1.62 g, 10.0 mmoL) and a few crystals of 4-N,N-dimethylaminopyridine followed by 15 mL of tetrahydrofuran. The reaction is then heated to 40°–45° C. for 1 hour. After the reaction mixture cools to room temperature, 1 mL of concentrated ammonium hydroxide is added via syringe. The reaction is stirred for 20 minutes and the resulting slurry filtered and the solid washed with tetrahydrofuran. The solid is dried in vacuo (60° C., <1 mm) to afford 1.72 g (79%) of N-phthaloyl-$\beta$-alanine amide, which can be alternatively named as 3-phthalimidopropionamide, as a white powder mp 252°–253° C.; $^1$H NMR (DMSO-d$_6$) $\delta$8.00–7.70 (m, 4H, Ar), 7.45 (br s, 1H, CONH$_2$), 6.89 (br s, 1H, CONH$_2$), 3.78 (t, 2H, J=7 Hz, CH$_2$CO), 2.43 (t, 2H, CH$_2$); $^{13}$C NMR (DMSO-d$_6$) $\delta$171.5, 167.6, 134.2, 131.6, 122.9, 34.1, 33.5. Anal. Calcd for C$_{11}$H$_{10}$N$_2$O$_3$. Theoretical: C, 60.55; H, 4.62; N, 12.84. Found: C, 60.49; H, 4.59; N, 12.82.

EXAMPLE 9

To a stirred solution of glycinamide hydrochloride (2.20 g, 20.0 mmoL) and sodium carbonate (2.54 g, 24 mmoL) in 25 mL of water is added N-carbethoxyphthalimide (4.38 g, 20.0 mmoL). The resulting suspension is stirred for 1.5 hour and then filtered to afford 3.22 g (79%) of the crude product as a white powder. The crude product is slurried in 200 mL of refluxing ethanol. The resulting suspension after cooling to room temperature is filtered and the solid dried in vacuo (60° C., <1 mm) to afford 2.65 g (65%) of N-phthaloylglycinamide as a white powder: mp 199°–201° C.; $^1$H NMR (DMSO-$d_6$) δ8.00–7.8 (m, 4H, Ar), 7.70 (br s, 1H, $CONH_2$), 7.26 (br s, 1H, $CONH_2$), 4.16 (s, 2H, $CH_2$); $^{13}$C NMR (DMSO-$d_6$) δ167.8, 167.5, 134.4, 131.7, 123.1, 39.9. Anal. Calcd for $C_{11}H_{10}N_2O_3$. Theoretical: C, 60.55; H, 4.62; N, 12.84. Found: C, 60.49; H, 4.59 ; N, 12.82.

EXAMPLE 10

To a stirred solution of L-glutamine (43.8 g, 300 mmoL) and sodium carbonate (33.4 g, 315 mmoL) in 750 mL of water is rapidly added N-carbethoxyphthalimide [65.8 (97% pure, 67.8 g), 300 mmoL] as a solid. After 1 hour, the reaction mixture is filtered to remove unreacted N-carbethoxyphthalimide. The pH of the stirred filtrate is adjusted to 3–4 with 4N hydrochloric acid. The mixture is then seeded with N-phthaloyl-L-glutamine and the pH adjusted to 1–2 with 4N hydrochloric acid. The resulting slurry is stirred for 1 hour. The slurry is filtered and the solid washed with copious amounts of water. The solid is air-dried and then dried in vacuo (60° C., <1 mm) overnight to afford 49.07 g (59%) of N-phthaloyl-L-glutamine, which can be alternatively named as 2-phthalimidoglutaramic acid, as a white powder.

EXAMPLE 11

A stirred mixture of N-phthaloyl-L-glutamine (48.0 g, 174 mmoL), carbonyldiimidazole (30.43 g, 188 mmoL), and 4-dimethylaminopyridine (0.105 g, 0.861 mmoL) in anhydrous tetrahydrofuran (300 mL) is heated to reflux for 16 hours. The reaction slurry is filtered and the solid washed with methylene chloride (200 mL). The solid is air-dried and then dried in vacuo (60° C., <1 mm) to afford 40.40 g (90%) of thalidomide as a white powder. $^1$H NMR (DMSO-$d_6$) δ11.16 (s, 1H, NH), 8.05–7.80 (br s, 4H, Ar), 5.18 (dd, 1H, J=12, 5 Hz, CHCO), 3.05–2.85 (m, 1H, $CH_2CO$), 2,70–2.45 (m, 2H, $CH_2CH_2$) 2.15–2.00 (M, 1H, $CH_2$). $^{13}$C NMR (DMSO-$d_6$) δ172.8, 169.8, 167.1, 134.9, 131.2, 123.4, 49.0, 30.9, 22.0.

EXAMPLE 12

By employing (R)-phenylglycine in the procedure of Example 5, there is obtained (R)-α-phthalimidophenylacetic acid, as a white powder: mp 175°–177° C.; $^1$H NMR (DMSO-$d_6$, 250M Hz) δ12.50 (br s, 1H), 7.95–7.85 (m, 4H), 7.55–7.28 (m, 5H), 6.04 (s, 1H); 13C NMR (DMSO-$d_6$) δ168.9, 166.9, 135.0, 134.9, 131.0, 129.1, 128.1, 127.9, 123.5, 56.1. Anal. Calculated for $C_{16}H_{11}NO_4$. Theoretical: C, 68.32; H, 3.94; N, 4.98. Found: C, 68.32; H, 3.85; N, 4.95.

Likewise from (S)-phenylglycine, there is obtained (S)-α-phthalimidophenylacetic acid as a white powder: mp 180°–184° C.; $^1$H NMR (DMSO-$d_6$, 250M Hz) δ12.5 (br s, 1H), 7.95–7.85 (m, 4H), 7.55–7.28 (m, 5H), 6.04 (s, 1H); 13C NMR (DMSO-$d_6$) δ168.9, 166.9, 135.0, 134.9, 130.9, 129.1, 128.1, 127.9, 123.5, 55.1. Anal. Calculated for $C_{16}H_{11}NO_4$. Theoretical: C, 68.32; H, 3.94; N, 4.98. Found: C, 68.14; H, 3.87; N, 4.96.

EXAMPLE 13

To a stirred solution of N-phthaloylglycine (2.50 g, 8.89 mmol) in tetrahydrofuran (50 mL) is added carbonyldiimidazole (1.50 g, 9.25 mmol) and a few crystals of 4-N,N-dimethylaminopyridine. The reaction is then heated to 50° C. for 45 minutes. After the reaction mixture had cooled to room temperature, 1 mL of concentrated ammonium hydroxide is added via syringe. The reaction is stirred for 1 hour, then diluted with 50 mL of water and partially concentrated to remove the majority of the tetrahydrofuran. The resulting slurry was filtered and the solid washed with copious amounts of water. The solid was dried in vacuo (60° C., <1 mm) to afford 1.9 g (76%) of α-phthalimidophenylacetamide as an off-white powder: mp 218°–220° C.; 1H NMR (DMSO-$d_6$) δ9.00–7.75 (m, 4H, Ar), 7.61 (br s, 1H, $CONH_2$), 7.55–7.20 (m, 6H, Ar, $CONH_2$), 5.82 (s, 1H, $CHCO_2$); 13C NMR (DMSO-$d_6$) δ168.2, 167.1, 135.6, 134,5, 131.4, 129.4, 127.9, 127.7, 123.1, 56.3.

EXAMPLE 14

By following the procedure of Example 8 but utilizing an equivalent amount of 4-aminobutyric acid, there is obtained a 67% yield of 4-phthalimidobutyric acid as a white powder: mp 108°–111° C.; 1HNMR (DMSO-$d_6$) δ12.10 (s, 1H), 7.92–7.75 (m, 4H, Ar), 3.62 (t, J=6.8 Hz, 2H), 2.29 (t, J=7.2 Hz, 2H), 1.90–1.76 (m, 2H); 13C NMR (DMSO-$d_6$) δ173.8, 167.9, 134.2, 131.6, 122.9, 36.8, 30.9, 23.3.

EXAMPLE 15

By following the procedure of Example 15 but utilizing an equivalent amount of 4-phthalimidobutyric acid, there is obtained 4-phthalimidobutyramide as a white powder in a 23% yield: mp 159.5°–161.5° C.; 1H NMR (DMSO-$d_6$) δ8.0–7.7 (m, 4H, Ar), 3.58 (t, J=6.9 Hz, 2H), 2.09 (t, 2H), 1.92–1.70 (m, 2H); 13C NMR (DMSO-$d_6$) δ173.3, 167.9 134.2, 131.6, 122.9, 37.1.32.3, 23.9.

EXAMPLE 16

By following the procedure of Example 19 but employing N-carbethoxyphthalimide and (S)-phenylalaninamide hydrochloride, there is obtained (S)-2-phthalimido-3-phenylpropionamide which can be recrystallized from ethanol to afford white crystals: mp 211°–215° C.; 1H NMR (DMSO-$d_6$) δ7.92 (s, 5H, Ph), 7.72, 7.33 (2 s, 2H), 7.2–7.0 (m, 4H, Ar), 4.92 (dd, 1H, J=12, 4.5 Hz), 3.52 (dd, 1H, J=4.3, 13.9), 3.35 (dd, 1H, J=12, 13.9); 13C NMR (DMSO-$d_6$) δ169.6, 167.4, 137.7, 134.3, 131.2, 128.5, 128.1, 126.3, 122.9, 54.2, 33.7.

EXAMPLE 17

To a stirred solution of d,l-phenylalanine (4.17 g, 25.0 mmol) and sodium carbonate (2.78 g, 26.25 mmol) in 50 mL of water is added N-carboethoxyphthalimide (5.65 g, 25.0 mmol). The resulting slurry is stirred for 1.5 hour and filtered. The pH of the filtrate is adjusted to 1–2 with 4N hydrochloric acid with stirring. After 20 minutes, the slurry is refiltered and the solid washed with water. The solid is dried in vacuo (60° C., <1 mm) to afford 5.44 g (74%) of 2-phthalimido-3-phenylpropionic acid as a white powder: mp 165°–169° C.; 1H NMR (DMSO-$d_6$, 250M Hz) δ12.5(br s, 1H), 7.84(s, 4H), 7.23–7.06 (m, 5H), 5.13 (dd, 1H, J=5.0), 3.26–3.05 (m, 2H); 13C NMR (250 MHz, (DMSO-d6) δ170.0, 167.0, 137.2, 134.8, 130.6, 128.6, 128.2, 126.5, 123.3, 52.8, 33.8. Anal. Calculated for $C_{17}H_{13}NO_4$. Theoretical: C, 69.15; H, 4.44; N, 4.74. Found: C, 69.07; H, 4.34; N, 4.78.

EXAMPLE 18

To a stirred solution of 2-phthalimido-3-phenylpropionic acid (2.95 g, 10.0 mmol) in tetrahydrofuran (25 mL) are added carbonyldiimidazole (1.62 g, 10.0 mmol) and a few crystals of 4-N,N-dimethylaminopyridine, followed by 15 mL of tetrahydrofuran. The reaction mixture is stirred at room temperature for 45 minutes and 1 mL of concentrated ammonium hydroxide then is added. After 10 minutes, the reaction mixture is diluted with 50 mL water and the resulting slurry is partially concentrated to remove the tetrahydrofuran and filtered. The solid is washed with water and dried in vacuo (60° C., <1 mm) to afford 2.46 g (84%) of 2-phthalimido-3-phenylpropionamide as a white powder: mp 224°–226° C.; 1H NMR (DMSO-$d_6$, 250 MHz) $\delta$7.79 (s, 4H, Ar), 7.71 (br s, 1H, CONH2), 7.32 (br s, 1H, CONH2), 7.20–7.02 (m, 5H, Ar), 5.06–4.98 (m, 1H), 3.56–325 (m 2H); 13C NMR (DMSO-$d_6$, 250 MHz)d: 169.6, 168.0, 137,1, 134.3, 131.2, 129.5, 128.1, 126.3, 122.9, 54.2, 33.7. Anal. Calculated for $C_{17}H_{14}N_2O_3$. Theoretical: C, 69.38; H,4.79; N, 9.52. Found: C, 69.37; H, 4.73; N, 9.43.

EXAMPLE 19

To a stirred solution of 4-fluorophenylglycine (3.38 g, 20.0 mmol) and sodium carbonate in 450 mL of 2:1 water-:acetonitrile is added N-carbethoxyphthalimide (4.38 g, 20 mmol). After 1 hour, the reaction mixture is partially concentrated to remove the acetonitrile. The resulting slurry is filtered and the pH of the stirred filtrate is adjusted to 1–2 with 4N hydrochloric acid and then stirred for an additional 30 minutes and filtered. The solid is air-dried and then dried in vacuo (60° C., <1 mm) to afford 4.55 g (76%) of $\alpha$-phthalimido4-fluorophenylacetic acid as a white powder: mp 180°–183° C.; 1H NMR (DMSO-$d_6$, 250 MHz) $\delta$8.10–7.80 (m, 4H), 7.65–7.45 (m, 4H), 7.3–7.10 (t, 2H) 610 (s, 1H); 13C NMR (DMSO-$d_6$, 250 MHz) $\delta$168.9, 166.9, 163.6, 159.7, 135.0, 131.4, 131.3 (m), 130.9, 123.5, 115.0, 114.7, 54.4. Anal. Calculated for $C_{16}H_{10}NO_4F$. Theoretical C, 64.22; H, 3.37; N, 4.68. Found: C, 64.13; H, 3.33; N, 4.63.

Similarly prepared from 2-fluorophenylglycine is $\alpha$-phthalimido-2-fluorophenylacetic acid as a white solid: mp 174.5°–180.5° C.; 1H NMR (DMSO-$d_6$) $\delta$13.8 (br s, 1H), 7.65–7.15 (m, 4H), 6.18 (s, 1H); 13C NMR (DMSO-$d_6$) $\delta$168.1, 166.8, 162.1, 158.2, 135.0, 130.9, 130.8, 130.5, 130.4, 124.1. 123.6, 121.8, 121.6, 115.3, 114.9, 48.9. Anal. Calculated for $C_{16}H_{10}NO_4F$. Theoretical: C, 64.22; H, 3.37; N, 4,68. Found: C, 63.93; H, 3.27; N, 4.68.

EXAMPLE 20

Similarly prepared according to the procedure of Example 18 from $\alpha$-phthalimido-4-fluorophenylacetic acid, carbonyldiimidazole, 4-N,N-dimethylaminopyridine and concentrated ammonium hydroxide is $\alpha$-phthalimido-4-fluorophenylacetamide which can be recrystallized from tetrahydrofuran to afford 0.76 g (51%) of the product as white crystals: mp 180°–183° C; 1H NMR (DMSO-$d_6$) $\delta$8.00–7.55 (m, 4H), 7.64 (s, 1H), 7.60–740 (m, 3H), 7.25–7.05 (m, 2H), 5.83 (s, 1H). Anal. Calculated for $C_{16}H_{11}N_2O_3F$. Theoretical: C, 64.43; H, 3.72; N, 9.39. Found: C, 64.16; H, 3.62; N, 9.18.

Likewise from $\alpha$-phthalimido-2-fluorophenylacetic acid there is obtained $\alpha$-phthalimide 2-fluorophenylacetamide as small white crystals: mp 197°–201° C.; 1H NMR (DMSO-$d_6$) $\delta$8.05–7.75 (m, 5H), 7.65–7.05 (m, 5H), 6.06 (s, 1H), 13C NMR (DMSO-$d_6$) $\delta$167.4, 166.9, 162.2, 158.3, 134.6, 131.3, 131.2, 131.1, 130.2, 130.0, 123.9, 123.8, 123.2, 122.4, 115.1, 114.8, 49.9.

EXAMPLE 21

To a stirred solution of d,l-leucine (3.31 g, 25.0 mmol) and sodium carbonate (2.78 g, 26.25 mmol) in 50 mL of water is added N-carboethoxyphthalimide (5.65 g, 25.0 mmol). After 1 hour at room temperature, the reaction slurry is filtered, the filtrate stirred, and the pH adjusted to 1–2 with 4N hydrochloric acid. The mixture is stirred overnight, the resulting slurry is filtered, and the solid washed with water and dried in vacuo (60° C., <1 mm) to afford 5.32 g (81%) of the 2-phthalimido-4-methylpentanoic acid as a white powder: mp 134°–137° C.; 1H NMR (DMSO-$_6$, 250M Hz) $\delta$12.50 (br s, 1H), 8.00–7.80 (m, 4H), 4.79 (dd, 1H, J=4.3), 2.28–2.10 (m, 1H), 1.94–1.77 (m, 1H), 0.89 (d, 3H, J=4.4), 0.86 (d, 3H, J=4.5); 13C NMR (DMSO-$d_6$) $\delta$170.8, 167.4, 134.8, 131.1, 123.3, 50.2, 36.7, 24.6, 23.0, 20.8. Anal. Calculated for $C_{14}H_{15}NO_4$. Theoretical: C, 64.36; H, 5.74; N, 5.36. Found: C, 64.18; H, 5.73; N, 5.98.

EXAMPLE 22

To a stirred solution of 2-phthalimido-4-methylpentanoic acid (1.32 g, 5.0 mmol) in tetrahydrofuran (25 mL) are added carbonyldiimidazole (0.81 g, 5.0 mmol) and a few crystals of 4-N,N-dimethylaminopyridine followed by 15 mL of tetrahydrofuran. The reaction mixture is stirred at room temperature for 1 hour, then 1 mL of concentrated ammonium hydroxide is added. After 10 minutes, the reaction mixture is diluted with 50 mL water. The resulting slurry is partially concentrated to remove the tetrahydrofuran and filtered. The solid is washed with water and dried in vacuo (60° C., <1 mm) to afford 1.16 g (89%) of 2-phthalimido-4-methylpentanamide as a white powder: mp 173°–176° C.; 1H NMR (DMSO-$_6$, 250 MHz) $\delta$7.95–7.79 (m, 4H, Ar), 7.61 (br s, 1H, CONH2), 7.22 (br s, 1H, CONH2), 4.73–4.60 (m, 1H), 2.30–2.10 (m, 1H), 1.95–1.80 (m, 1H), 1.45–1.25 (m, 1H); 13C NMR (DMSO-$d_6$) d: 170.4, 167.7, 134.4, 131.5, 123.1, 51.3, 36.4, 24.7, 23.2, 20.6. Anal. Calculated for $C_{14}H_{16}N_2O_3$. Theoretical: C, 64.60; H, 6.20; N, 10.76. Found: C, 64.63; H, 6.11; N, 10.70.

EXAMPLE 23

To a stirred solution of histidine (3.17 g, 20.0 mmol) and sodium carbonate (2.23 g, 21 mmol) in 50 mL of water is added N-carboethoxyphthalimide (4.52 g, 20.0 mmol). After 1.5 hour, the reaction slurry is filtered. The filtrate is stirred and the pH adjusted to 1–2 with 4N hydrochloric acid. The resulting slurry is filtered and the solid washed with water and dried m vacuo (60 C, <1 mm) to afford 3.65 g (64%) of 2-phthalimido-3-(imidazol-4-yl)propionic acid as a white powder: mp 280°–285° C.; 1H NMR (DMSO-$_6$, 250M Hz) $\delta$12.5 (br s, 1H), 7.90–7.60 (m, 6H), 6.80(s, 1H), 4.94 (t, 1H, J=7.8), 3.36 (d, 2H, J=7.8); 13C NMR (DMSO-$d_6$) $\delta$170.1, 167.1, 134.8, 134.6, 133.2, 131.1, 123.2, 116.3, 52.4, 25.8; Anal. Calculated for $C_{14}H_{11}N_3O_4$. Theoretical: C, 58.95; H, 3.89; N, 14.73. Found: C, 58.80; H, 3.88; N, 14.66.

EXAMPLE 24

To a stirred mixture of 3-amino-3-(4-methoxyphenyl) propionic acid (1.95 g, 10.0 mmol) and sodium carbonate (1.11 g, 10.5 mmol) in 200 mL of acetonitrile-water 1:1 is added N-carboethoxyphthalimide (2.26 g, 10.0 mmol). After 1 hour, the reaction slurry is filtered. The filtrate is concentrated to remove the acetonitrile and the pH adjusted to 1–2 with 4N hydrochloric acid and stirred over night. The resulting slurry is filtered and the solid washed with water. The solid is dried in vacuo (60 C, <1 mm) to afford 2.82 g (87%) of 3-phthalimido-3-(4-methoxyphenyl)propionic acid as a white powder: mp 160°–164° C.; 1H NMR (DMSO-$_6$, 250 MHz) $\delta$12.5 (br s, 1H), 7.95–7.80 (m, 4H), 7.36 (d, 2H, J=8.7), 6.92 (d, 2H, J=8.4 Hz), 5.18–5.10 (m, 1H), 3.70–3.15

(m, 2H); 13C NMR (DMSO-d$_6$) δ171.7, 167.6, 158.6, 134.6, 131.0, 130.8, 128.3, 123.1, 113.9, 55.0, 49.6, 35.9. Anal. Calculated for C$_{18}$H$_{15}$NO$_5$. Theoretical: C, 66.46; H, 4.63; N, 4.31. Found: C, 66.25; H, 4.65; N, 4.28.

Similarly from 3-amino-3-(3-methoxyphenyl)propionic acid there is obtained 3-phthalimido-3-(3-methoxyphenyl) propionic acid as white crystals: mp 111°–115° C.; 1H NMR (DMSO-$_6$, 250 MHz) δ12.5 (br s, 1H), 7.94–7.81 (m, 4H), 7.32–7.23 (m, 1H), 7.02–6.85 (m, 3H), 5.70–5.60 (m, 1H), 3.77–3.67 (s, 3H), 3.56–3.15 (m, 2H); 13C NMR (DMSO-d$_6$) δ171.6, 167.6, 159.2, 140.4, 134.7, 131.0, 129.7, 123.2, 119.0, 112.9, 112.7, 54.9, 50.0, 35.8.

Likewise from 3-amino-3-(2-methoxyphenyl)propionic acid there is obtained 3-phthalimido-3-(2-methoxyphenyl) propionic acid as a white powder: mp 163°–168° C; 1H NMR (DMSO-$_6$, 250 MHz) δ12.5 (br s, 1H), 7.95–7.80 (m, 4H), 7.45–6.90 (m, 4H), 6.05–5.92 (m, 1H), 3.78 (s, 3H) 3.55–3.05 (m, 2H); 13C NMR (DMSO-d$_6$) δ171.7, 167.5, 156.1, 134.5, 131.0, 128.9, 127.3, 126.1, 123.0, 120.1, 111.0, 55.5, 45.3, 35.1.

EXAMPLE 25

By following the procedure of Example 22 utilizing 3-phthalimido-3-(4-methoxyphenyl)propionic acid, there is obtained 3-phthalimido-3-(4-methoxyphenyl)propionamide as a white powder: mp 183°–188° C.; 1H NMR (DMSO-$_6$, 250 MHz) δ7.90–7.75 (m, 4H, Ar), 7.58 (br s, 1H, CONH$_2$), 7.38 (d, 2H, J=8.6), 6.91 (d 3H, J=8.6), 5.73 (t, 1H, J=7.8), 3.23(d, 2H, J=7.9); 13C NMR. (DMSO-d$_6$)d: 171.2, 167.6, 158.5, 134.5, 131.3, 131.2, 128.4, 123.0, 113.7, 55.0, 49.9, 36.8.. Anal. Calculated for C$_{18}$H$_{16}$N$_2$O$_4$. Theoretical: C, 66.66; H,4.97; N, 8.64. Found: C, 66.27; H, 5.04; N, 8.40.

EXAMPLE 26

To a stirred mixture of 3-amino-3-(4-cyanophenyl) propionic acid (3.80 g, 20.0 mmol) and sodium carbonate (2.23 g, 21 mmol) in 100 mL of water is added N-carboethoxyphthalimide (4.52 g, 20.0 mmol). After 2 hour, the reaction slurry is filtered and the pH of the stirred filtrate adjusted to 1–2 with 4N hydrochloric acid. The resulting gel is extracted with ethyl acetate (3×30 mL). The extract is dried over magnesium sulfate and concentrated in vacuo. The crude product is recrystallized from 10% aqueous acetonitrile and then recrystallized from 20% aqueous methanol. The product is dried in vacuo (60° C., <1 mm) to afford 1.5 g (23%) of 3-phthalimido-3-(4-cyanophenyl) propionic acid as a white powder: mp 134°–137° C.; 1H NMR (DMSO-$_6$, 250 MHz) δ12.5 (br s, 1H), 7.95–7.56 (m, 8H),.5.76 (t, 1H, J=7.7), 3.57–3.15 (m, 2H); 13C NMR (DMSO-d$_6$) δ171.5, 167.6, 144.2, 134.8, 132.6, 131.1, 128.1, 123.3, 118.5, 49.7, 35.5.

Likewise from 3-amino-3-(3-cyanophenyl)propionic acid there is obtained 3-phthalimido-3-(3-cyanophenyl)propionic acid as a white powder: mp 172°–175° C.; 1H NMR (DMSO-$_6$, 250 MHz) δ12.5 (br s, 1H), 8.05–7.51 (m, 8H), 5.82–5.70 (m, 1H), 3.63–3.20(m, 2H); 13C NMR (DMSO-d$_6$) δ171.5, 167.6, 140.3, 134.6 132.0, 131.5, 131.2, 130.7, 129.8, 123.22, 118.5, 111.6, 49.3, 35.6.

EXAMPLE 27

By following the procedure of Example 22 utilizing 3-phthalimido-3-(4-cyanophenyl)propionic acid, there is obtained 3-phthalimido-3-(4-cyanophenyl)propionamide as a white powder: 1H NMR (DMSO-$_6$, 250 MHz) δ8.05–7.50 (m, 9H), 6.97 (s, 1H), 5.87–5.72 (m, 1H), 3.44–3.12 (m, 2H); 13C NMR (DMSO-d$_6$) δ170.8, 167.6, 144.6, 134.6, 132.4, 131.1, 127.9, 123.2, 118.5, 110.3, 49.8, 36.4.

Similarly from 3-phthalimido-3-(3-cyanophenyl) propionic acid (1.60 g, 5.0 mmol), there is obtained 3-phthalimido-3-(3-cyanophenyl)propionamide as a white powder: mp 217°–220° C.; 1H NMR (DMSO-$_6$, 250 MHz) δ8.05–7.40 (m, 9H), 6.99 (br s, 1H), 5.90–5.75 (m, 1H), 3.50–3.10 (m, 2H); 13C NMR (DMSO-d$_6$) d: 171.0, 167.7, 140.8, 134.6, 132.2, 131.5, 131.4, 130.8, 129.9, 123.2, 118.7, 111.5, 49.7, 36.7.

EXAMPLE 28

To a stirred solution of phenyl isocyanate (2.2 mL, 2.4 g, 20 mmol) in acetonitrile (40 mL) is added a solution of L-glutamine (2.92 g, 20.0 mmol) and sodium hydroxide (20 mmol) in water (20 mL). The reaction mixture is stirred for 45 hours, partially concentrated to remove the acetonitrile, and washed with ethyl acetate (2×25 mL). The pH of the aqueous layer is adjusted to 1–2 with 4N hydrochloric acid, the resulting thick slurry filtered, and the solid washed with water and air-dried to afford 4.70 g (89%) yield of 2-(N-phenyluriedo)-4-carbamoylbutyric acid as a white powder.

2-(N-phenyluriedo)-4-carbamoylbutyric acid (2.00 g, 7.54 mmol) and carbonyldiimidazole (1.24 g, 7.95 mmol) in tetrahydrofuran (30 mL) are heated at reflux for 16 hours. The reaction mixture is concentrated and the residue slurried in water (25 mL), the slurry filtered, and the solid washed with water and air-dried to afford 0.63 g of N-phenyl-N'-(1, 6-dioxopiperidin-2-yl)urea. After sitting, filtration of the filtrate afforded 0.70 g (38%) of the product as a white flocculent powder: 1H NMR (DMSO-d$_6$) δ8.51 (s, 1H, CONHCO), 7.6–7.2 (m, 6H, Ar, ArNH), 6.83 (s, 1H, NHCH), 4.26 (t, 1H, CHCO), 2.4–1.8 (m, 4H, CH$_2$CH$_2$); 13C NMR (DMSO-d$_6$) δ173.2, 155.6, 132.2, 128.7, 127.7, 126.7, 55.7, 29.8, 27.2. Anal. Calculated for C$_{12}$H$_{13}$N$_3$O$_3$. Theoretical: C, 58.29; H, 5.29; N, 16.99. Found: C, 58.12; H, 5.17; N, 17.02.

EXAMPLE 29

To a stirred solution of 3-amino-3-(4-methoxyphenyl) propionic acid methyl ester hydrochloride (1.50 g, 6.1 mmol) and sodium carbonate (90.65 g, 6.1 mmol) in 40 mL of water was added N-carboethoxyphthalimide (1.34 g, 6.1 mmol) in 12 mL of acetonitrile. The reaction mixture was stirred at room temperature for 1 hour. The reaction mixture was partially concentrated and this mixture was stirred for 72 hours. The resulting slurry was filtered and the solid was washed with copious amount of water. The solid was dried in vacuo (30° C., <1 mm) to afford 1.70 g (50%) of methyl 3-phthalimido-3-(4-methoxyphenyl)propionate as a white powder. mp 65°–66° C.; 1H NMR (DMSO-$_6$, 250 MHz) δ7.83–7.91 (m, 4H), 6.88–7.3 (m, 4H), 5–80 (dd, 1H, J=7.5, 2.5), 372 (S, 3H), 3.54 (3, 3H), 3.2–3.6 (m, 2H); 13C NMR (DMSO-d$_6$) δ170.7, 167.5, 158.7, 134.6, 131.0, 130.5, 128.3, 123.2, 113.9, 55.0, 51.5, 49.4, 35.4. Anal. Calcd for C$_{19}$H$_{17}$NO$_5$: C, 67.25; H, 5.05; N, 4.13; Found: C, 66.96; H, 5.00; N, 4.11.

EXAMPLE 30

To a stirred solution of 3-amino-3-(4-methoxyphenyl) propionic acid ethyl ester hydrochloride (1.00 g, 3.85 mmol) and sodium carbonate (0.41g, 3.85 mmol) in 40 mL of water was added N-carboethoxyphthalimide (0.84 g, 3.85 mmol) in 10 mL of acetonitrile. The reaction was complete in one hour by TLC. The reaction mixture was partially concentrated to remove the acetonitrile. To the resulting mixture was added 0.5 mL of ethyl ether and the mixture was stirred for 1 hour at room temperature. The resulting slurry was filtered and the solid was washed with copious amounts of water. The solid was air-dried overnight to afford 1.02 g (75%) of ethyl 3-phthalimido-3-(4-methoxyphenyl) propionate as a white gum: mp 32° C.; 1H NMR (DMSO-$_6$, 250 MHz) δ7.86 (m, 4H), 6.90–7.37 (M, 4H), 5.66 (dd, 1H J1=7.5, J2 =2.5), 4.00 (d, 2H, J=7.5), 3.3–3.6 (M, 2H), 1.04 (t, 3H, J=7.5 Hz); 13C (DMSO-d$_6$) δ170.1, 167.5, 158.7, 134.7, 131.0, 130.5, 128.3, 123.2, 113.88, 60.1, 55.0, 49.5, 35.7, 13.8. Anal. Calcd for $C_{20}H_{19}NO_5$: C, 67.98; H, 5.42; N, 3.90; Found C, 67.78; H, 5.30; N, 3.92.

EXAMPLE 31

To a stirred solution of 3-amino-3-phenylpropionic acid methyl ester hydrochloride (0.50 g, 2.3 mmol) and sodium carbonate (0.25 g, 2.3 mmol) in 10 mL of water was added N-carboethoxyphthalimide (0.51 g, 2.3 mmol) in 7 mL of acetonitrile. The reaction progress was monitored by TLC (ethyl acetate/hexane; 1:2) which showed that the reaction was complete in one hour. The reaction mixture was partially concentrated to remove the acetonitrile. The resulting slurry was filtered and the solid was washed with 20 mL of water. The solid was dried in vacuo (60° C., <1 mm) to afford 280 mg (39.4%) of methyl 3-phthalimido-3-phenylpropionate as a white powder: mp 75°–76° C.; 1H NMR (DMSO-$_6$, 250 MHz) δ7.26–7.83 (m, 9H), 5.68–5.75 (m, 1H), 3.55 (S, 3H), 3.37–3.66 (m, 2H); 13C NMR (DMSO-d$_6$) δ170.7, 167.6, 138.6, 134.7, 131.0, 128.6, 127.8, 126.9, 123.3, 51.6, 49.9, 35.3. Anal. Calcd for $C_{18}H_{15}NO_4$: C, 69.89; H, 4.89; N, 4.53; Found: C, 69.69; H, 4.83; N, 4.49.

EXAMPLE 32

To a stirred solution of 3-amino-3-(4-methoxyphenyl) propionic acid propyl ester hydrochloride (1.50 g, 5.52 mmol) and sodium carbonate (0.59g, 5.52 mmol) in 50 mL of water was added N-carboethoxy-phthalimide (1.21 g, 5.52 mmol) in 12 mL of acetonitrile. The reaction was complete in one hour. The acetonitrile was removed in vacuo and 5 mL of ether was added to the mixture, which was stirred overnight at room temperature. The resulting slurry was filtered and the solid was washed with 60 mL of water. The solid was dried in vacuo (24° C., <1 mm) to afford 1.69 g (83.2%) of propyl 3-phthalimido-3-(4-methoxyphenyl) propionate as a white powder: mp 51.2°–52.8° C.; 1H NMR (DMSO-d$_6$250 MHz) δ7.86 (m, 4H), 6.92–7.33 (m, 4H), 5.66 (dd, 1H, J1=7.5, 2.5 Hz), 3.90 (t, 2H, J=5 Hz), 3.72 (S, 3H), 3.3–3.63 (m, 2H), 1.42 (hex, 2H, J=7.5 Hz), 0.75 (t, 3H, J=7.5 Hz); 13C (DMSO-d$_6$) δ170.2, 167.5, 158.7, 134.7, 131.0, 130.5, 128.3, 123.2, 113.9, 65.6; 55.0, 49.5, 21.3, 9.98. Anal. Calcd for $C_{19}H_{17}NO_5$:=C, 68.65; H, 5.76; N, 3.81; Found=C, 68.42; H, 5.49; N, 3.76.

EXAMPLE 33

A stirred mixture of phenylglycine (1.51 g, 10.0 mmol) and phthalic dicarboxaldehyde (1.34 g, 10.0 mmol) in 10 mL of acetic acid under nitrogen was heated to reflux for 10 minutes. The resulting mixture was allowed to cool overnight and the resulting slurry filtered to afford 1.56 g of crude product. The crude product was recrystallized from acetic acid to afford after drying in vacuo (<1 mm, 60 C.) 0.95 g (36%) of α-(1-oxoisoindolin-2-yl)phenylacetic acid as a white powder: 1H NMR (DMSO-$_6$, 250 MHz) 7.85–7.30 (m, 9H, Ar), 6.01 (s, 1H, CH), 4.64 (d, J=17.4 Hz, 1H), 3.92 (d, J=17.4H, 1H); 13C NMR (DMSO-d$_6$) 171.2, 167.4, 142.0, 134.6, 131.6, 131.3, 128.9, 128.7, 128.4, 127.9, 123.6, 122.9, 57.9, 47.6; Anal. Calcd for $C_{16}H_{13}NO_3$ 0.13 $H_2O$. Theory: C, 71.29; h, 4.95; N, 5.20. Found: C, 71.29; h, 4.86; N, 5.26.

EXAMPLE 34

A mixture of α-(1-oxoisoindolin-2-yl)phenylacetic acid (0.50 g, 1.87 mmol) and carbonyl diimidazole (CDI, 0.319 g, 1.96 mmol) in 20 mL of tetrahydrofuran under nitrogen was stirred for 2.5 h, then 0.3 mL of 15N ammonium hydroxide was added. The resulting mixture was stirred for 20 minutes, concentrated to an oil and diluted with 25 mL of water. The mixture was stirred and the resulting slurry filtered to afford after drying 0.38 g (76%) of α-(1-oxoisoindolin-2-yl)phenylacetamide as a white powder: 1H NMR (DMSO-$_6$, 250 MHz) 8.10–7.20 (m, 11H), 6.03 (s, 1H), 4.80 (d, J=17.7 Hz, 1H), 3.90 (d, J=17.7 Hz, 1H); 13C NMR (DMSO-d$_6$) 167.4, 142.2, 136.0, 131.5, 131.4, 128.7, 128.5, 128.0, 127.7, 123.4, 122.8, 57.5, 48.0; Anal. Calcd for $C_{16}H_{14}N_2O_2$: Theory C, 72.17; H, 5.30; N, 10.52. Found: C, 72.00; H, 5.27; N, 10.56.

EXAMPLE 35

By following the procedure of Example 33 utilizing d,l-phenylalanine there is obtained, without recrystallization, 4.46 g (79%) of 3-phenyl-2-(1-oxoisoindolin-2-yl)propionic acid as an off-white solid: 1H NMR (DMSO-$_6$, 250 MHz) 13.16 (br s, 1H, COOH), 7.70–7.05 (m, 9H, Ar), 5.17 (dd, J=11, 4.8 Hz, 1H), 4.45 (s, 2H, benzylic H), 3.42 (dd, J=14.6, 4.8 Hz, 1H), 3.22 (dd, J=14.6, 11 Hz, 1H); 13C NMR (DMSO-d$_6$) 171.8, 167.7, 141.8, 137.4, 131.5, 131.4, 128.4, 128.3, 127.8, 126.4, 123.4, 122.8, 54.7, 47.2, 34.6; Anal. Calcd for $C_{17}H_{15}NO_3$: Theory C, 72.58; H, 5.37; N, 4.98. Found: C, 72.60; H, 5.33; N, 4.91.

EXAMPLE 36

By following the procedure of Example 34 utilizing 3-phenyl-2-(1-oxoisoindolin-2-yl)propionic acid there is obtained 1.13 g (81%) of 3-phenyl-2-(1-oxoisoindolin-2-yl)-propionamide as a fine white powder: 1H NMR (DMSO-$_6$, 250 MHz) 7.90–7.05 (m, 11 H, Ar and CONH$_2$), 5.16 (dd, J=11, 5 Hz, 1H), 5.71 (d, J=18 Hz, 1H), 5.45 (d, J=18 Hz, 1H), 3.33(dd, J=15, 5 Hz, 1H), 3.11 (dd, J=11, 15 Hz, 1H); 13C NMR(DMSO-d$_6$) 172.0, 167.6, 142.0, 137.6, 131.7, 131.3, 128.4, 128.2, 127.6, 126.3, 123.3, 122.7, 54.6, 47.2, 35.3; Anal. Calcd for $C_{17}H_{16}N_2O_2$: Theory C, 72.84; H, 5.75; N, 9.99. Found: C, 72.72; H, 5.76; N, 9.86.

EXAMPLE 37

By following the procedure of Example 33 utilizing 3-amino-3-phenylpropionic acid there is obtained 0.8 g of crude product. The filtrate was then concentrated and the residue slurried in ethyl acetate to afford an additional 1.39 g of crude product. The combined crude products were recrystallized from ethyl acetate to afford 1.52 (58%) of 3-phenyl-3-(1-oxoisoindolin-2-yl)propionic acid as fine white crystals: 1H NMR (DMSO-d$_6$, 250 MHz) δ12.44 (br s, 1H, CO$_2$H), 7.80–7.15 (m, 9H, Ar), 5.79 (overlapping dd, 1H), 4.54 (d, J=17.6 Hz, 1H), 4.15 (d, J=17.6 Hz, 1H), 3.35–3.0 (m, 2H); 13 C NMR (DMSO-d$_6$) 171.8, 166.9, 141.6, 139.3, 132.0, 131.4, 128.6, 127.9, 127.6, 127.0, 123.4, 122.8, 51.3, 46.3, 36.6; Anal. Calcd for $C_{17}H_{15}NO_3$: Theory C, 72.58; H, 5.37; N, 4.90. Found: C, 72.23; H, 5.29; N, 4.90.

EXAMPLE 38

To a stirred solution of 3-phenyl-3-(1-oxoisoindolin-2-yl) propionic acid (0.703 g, 2.50 mmol) in 15 mL of tetrahydrofuran under nitrogen was added carbonyldiimidazole (0.438 g, 2.70 mmol), and a few crystals of 4-N,N-dimethylaminopyridine [DMAP]. The reaction mixture was stirred for 1.5 hours and then 0.25 mL of 15N ammonium hydroxide was added. After 20 minutes, the reaction mixture was concentrated in vacuo and the residue slurried in water. The resulting solid was isolated by filtration and dried in vacuo to afford 0.58 g (80%) of crude product as an off-white powder. The crude product was recrystallized from ethanol to afford 0.403 g (57%) of 3-phenyl-3-(1-oxoisoindolin-2-yl)-propionamide as white prisms: 1H NMR (DMSO-$_6$, 250 MHz) 7.8–7.2 (m, 10H), 6.92 (br s, 1H), 5.81 (overlapping dd, 1H) 4.59 (d, J=17.5 Hz, 1H), 4.16 (d, J=17.5 Hz, 1 H), 3.1–2.8 (m, 2H); 13C NMR (DMSO-d$_6$) 171.3, 167.0, 140.7, 132.2, 131.4, 128.6, 127.9, 127.5, 126.9, 123.5, 122.8, 51.5, 46.3, 37.9; Anal. Calcd for $C_{17}H_{16}N_2O_2$: Theory C, 72.84; H, 5.75; N, 9.99. Found: C, 72.46; H, 5.68; N, 9.91.

EXAMPLE 39

By following the procedure of Example 33 utilizing 3-amino-3-(4-methoxyphenyl)-propionic acid there is obtained 1.52 g of crude product as an off white solid from the reaction mixture. The filtrate was concentrated and the residue slurried in 25 mL of ethyl acetate to afford after filtration an additional 1.27 g (41%) of crude product as a pale green powder. The combined crude products were recrystallized from 280 mL of ethyl acetate to afford after drying 1.69 g (55%) of 3-(4-methoxyphenyl)-3-(1-oxoisoindolin-2-yl)propionic acid as an off-white solid: 1H NMR (DMSO-$_6$, 250 MHz); 13C NMR (DMSO-d$_6$); Anal. Calcd for $C_{18}H_{17}NO_4$: Theory C, 69.44; H, 5.50; N, 4.50. Found: C, 69.33; H, 5.45; N, 4.49.

EXAMPLE 40

By following the procedure of Example 38 utilizing 3-(4-methoxyphenyl)-3-(1-oxoisoindolin-2-yl)propionic acid there is obtained 0.49 g (82%) of crude product. The crude product was recrystallized from ethyl acetate (40 mL) to afford 0.27 g (45%) of 3-(4-methoxyphenyl)-3-(1-oxoisoindolin-2-yl)propionamide as white needles: 1H NMR (DMSO-$_6$, 250 MHz) 7.8–7.4 (m, 5H), 7.29 (d, 2H, J=9 Hz), 6.91 (d, 2H, J=9 Hz), 5.78 (t, 1H, J=8 Hz), 4.55 (d, 1H, J=17.5 Hz), 4.11 (d, J=17.5 Hz, 1 H), 3.72(s, 3H), 3.05–2.75 (m, 2H); 13C NMR (DMSO-d$_6$) 171.2, 166.8, 158.4, 141.6, 132.2, 131.8, 131.2, 128.1, 127.8, 123.3, 122.7, 113.8, 55.0, 51.0, 46.1; Anal. Calcd for C18H18N2O3-0.38 H$_2$O: Theory C, 68.58; H, 5.99; N, 8.80. Found: C, 68.58; H, 5.86; N, 8.80.

EXAMPLE 41

The procedure of Example 33 is followed utilizing 3-amino-3-(3,4-dimethoxyphenyl)propionic acid with the following exceptions. The reaction mixture (solution) was concentrated to a thick oil which was diluted with 10 mL of ethyl acetate. The resulting slurry was filtered, the solid washed with ethyl acetate and then dried in vacuo (>1 mm, 60 C.) to afford 2.77 g (81%) of 3-(3,4-dimethoxyphenyl)-3-(1-oxoisoindolin-2-yl)propionic acid as a white powder: mp 146.5°–148.5° C.; 1H NMR (DMSO-$_6$, 250 MHz) 12.34 (br s, 1H, CO2H), 7.8–7.4 (m, 4H), 7.1–6.8 (m, 3H), 5.85–5.65 (m, 1H), 4.51 (d, 1H, J=18 Hz), 4.13 (d, 1H, J=18 Hz), 3.75 (s, 3H), 3.73 (s, 3H), 3.3–3.0 (m, 2H); 13C NMR (DMSO-d$_6$) 171.8, 166.7, 148.7, 148.3, 141.6, 132.1, 131.6, 131.3, 127.8, 123.4, 122.7, 119.2, 111.7, 111.2, 55.5, 55.4, 46.3, 36.8; Anal. Calcd for $C_{19}H_{19}NO_5$: Theory C, 66.85; H, 5.61; N, 4.10. Found: C, 67.19; H, 5.57; N, 3.73.

EXAMPLE 42

The procedure of Example 38 is followed utilizing 3-(3,4-dimethoxyphenyl)-3-(1-oxoisoindolin-2-yl)propionic acid with the following changes. The crude product did not precipitate from water immediately. The product crystallized from aqueous solution upon sitting for several days after an ether wash to afford 0.26 g (22%) of 3-(3,4-dimethoxyphenyl)-3-(1-oxoisoindolin-2-yl)propionamide as white needles: 1H NMR (DMSO-$_6$, 250 MHz) 7.8–7.4 (m, 5H), 7.1–6.85 (m, 4H), 5.76 (m, 1H), 4.57 (d, 17.6 Hz, 1H), 4.15 (d, J=17.6 Hz, 1H), 3.74 (s, 3H), 3.72 (s, 3H), 3.1–2.8 (m, 2H); 13C NMR (DMSO-d$_6$) 171.2, 166.8, 148.6, 148.1, 141.6, 132.2, 132.2, 131.2, 127.8, 123.4, 122.7, 119.0, 111.6, 111.0, 55.4, 51.4, 46.2, 37.9; Anal. Calcd for $C_{19}H_2ON_2O_4$: Theory C, 67.05; H, 5.92; N, 8.23. Found: C, 66.74; H, 5.88; N, 8.02.

EXAMPLE 43

To a stirred solution of 3-amino-3-(3,4-diethoxyphenyl) propionic acid (1.03 g, 4.07 mmol) and sodium carbonate (0.453 g, 4.27 mmol) in a 1/1 mixture of 150 mL of acetonitrile/water (heated to 45° C. to dissolve) was added N-carbethoxyphthalimide (0.89 g, 4.07 mmol). The reaction mixture was stirred 1 hour, then partially concentrated in vacuo to remove the acetonitrile to afford a pale yellow solution. The stirred solution was acidified to pH 0–1 with 4N hydrochloric acid to form a gum. The mixture was stirred overnight. The gum had not solidified and 1 mL of ether was added to mixture. The gum solidified on stirring and the slurry was filtered and the solid dried to afford 1.94 g (94%) of 3-(3,4-diethoxyphenyl)-3-phthalimidopropionic acid as a yellow solid: 1H NMR (DMSO-$_6$, 250 MHz) 12.41 (br s, 1H, COOH), 8.10–7.75 (m, 4H, Ar), 7.15–6.85 (m, 3H, Ar), 5.62 (overlapping dd, 1H), 4.20–3.90 (m, 4H, 2OCH2), 3.51 (dd, 1H, J=16.5, 9 Hz), 3.25 (dd, 1H, J=16.5, 7 Hz), 1.5–0.9 (m, 6H, 2 CH3) 13C NMR (DMSO-d$_6$) 1717, 167.6, 147.9, 147.8, 134.6, 131.3, 131.0, 123.1, 119.4, 113.2, 112.7, 63.8, 63.7, 50.0, 36.0, 14.6, 14.6; Anal. Calcd for $C_{21}H_{21}NO_6$: Theory C, 65.79; H, 5.52; N, 3.65. Found: C, 65.54; H, 5.55; N, 3.62.

EXAMPLE 44

The procedure of Example 43 was followed with the following changes. The reaction mixture concentrated in vacuo and to an oil which was diluted with water (20 mL) and ether (1 mL) and the mixture stirred overnight. The resulting slurry was filtered and the solid dried in vacuo to afford 0.41 g (41%) of crude product. The crude product was recrystallized from ethyl acetate to afford 0.265 g (27%) of 3-(3,4-diethoxyphenyl)-3-phthalimidopropionamide as white crystals: 1H NMR (DMSO-$_6$, 250 MHz) 8.00–7.60 (m, 4H, Ar), 7.55 (br s, 1H, NH), 7.03 (br s, 1H, NH), 6.89 (br s, 3H, Ar), 5.66 (t, 1H, J=8 Hz), 4.15–3.85 (m, 4H), 3.3–3.05 (m, 2H), 1.5–1.15 (m, 6H); 13C NMR (DMSO-d$_6$) 171.2, 167.6, 147.8, 147.6, 134.5, 131.6, 131.2, 123.0, 119.5, 113.0, 112.7, 63.7, 63.6, 50.2, 36.9, 14.6, 14.6; Anal. Calcd for $C_{21}H_{22}N_2O_5$: Theory C, 65.96H, 5.80; N, 7.33. Found: C, 65.45; H, 5.55; N, 7.20.

EXAMPLE 45

To a stirred solution of sodium carbonate (1.45 g, 13.7 mmol) in 500 mL of water-acetonitrile (1:1, v/v) was added 3-amino-3-(4-propoxyphenyl)propionic acid (3.05 g, 13.7 mmol) as a solid. The mixture was warmed to 30°–40° C. to dissolve the solids. The reaction mixture was allowed to cool to room temperature and N-carboethoxyphthalimide (3.00 g, 13.7 mmol) was added and the reaction mixture was stirred for one hour at room temperature. The reaction mixture was then partially concentrated to remove the acetonitrile and the pH of the resulting solution was adjusted to approximately 3 with 4N hydrochloric acid. The resulting slurry was stirred overnight and then filtered and the solid was washed with copious amounts of water. The solid was dried in vacuo (60° C., <1 mm) to afford 3.64 g (75%) of 3-phthalimido-3-(4-propoxyphenyl)propionic acid as a white powder: mp 142.5°–143.6° C., 1H NMR(DMSO-$d_6$, 250 MHz) δ12.43 (br s, 1H), 7.80–7.95 (m, 4H), 7.34 (d, 2H, J=9 Hz), 6.89 (d, 2H, J=9 Hz), 5.63 (overlapping dd, 1H), 3.88 (t, 2H, J=7 Hz), 3.45 (dd, 1H, J1=9 Hz, J2 =16.5 Hz), 3.30 (dd, 1H, J=7 Hz, J2=16.5 Hz), 1.60–1.85 (m, 2H), 0.95 (t, 3H, J=7 Hz); 13C (DMSO-$d_6$) δ171.8, 167.6, 158.6, 134.7, 131.1, 130.8, 128.3, 123.2, 114.4, 68.9, 49.7, 36.0, 22.0, 10.3; Anal. Calcd. for $C_{20}H_{19}NO_5$. Theoretical: C, 67.98; H, 5.42; N, 3.96. Found: C, 67.90; H, 5.40; N, 4.00.

EXAMPLE 46

To a stirred solution of 3-phthalimido-3(4-propoxyphenyl)propionic acid (1.41 g, 4.0 mmol) in 25 mL of under nitrogen was added carbonyldiimidazole (0.68 g, 4.2 mmol) followed by a catalytic amount of dimethylaminopyridine. The mixture was stirred for 45 minutes at room temperature. To the reaction mixture was then added concentrated ammonium hydroxide (0.29 mL, 4.4 mmol) and the reaction mixture was stirred for 30 minutes at room temperature. The mixture was then diluted with 10 mL of water and the tetrahydrofuran was removed in vacuo. The resulting slurry was filtered and the solid was washed with copious amounts of water. The solid was dried in vacuo (60° C., <1 mm) to afford 1.2 g of crude product. The crude product was purified by dissolving in 200 mL of ethyl acetate, stirring for 3 h and then concentrating to an 80 mL volume. The resulting slurry was filtered and the solid was washed with ethyl acetate (2×20 mL). The solid was air-dried to afford 0.513 g (36%) of 3-phthalimido-3-(4-propoxyphenyl)propionamide as a white powder: mp 109.5°–110.4° C.; 1H NMR (DMSO-$d_6$, 250 MHz) δ7.85 (br s, 4H), 7.55 (br s, 1H), 7.33 (d, 2H, J=8 Hz), 6.75–7.00 (m, 3H), 5.69 (t, 1H, J=8 Hz), 3.88 (t, 2H, J=6 Hz), 3.10–3.30 (m, 2H), 1.60–1.80 (m, 2H), 0.95 (t, 3H, J=7 Hz); 13C NMR (DMSO-$d_6$) δ171.2, 167.7, 158.0, 134.5, 131.23, 131.19, 128.4, 123.1, 114.3, 68.9, 49.9, 36.9, 22.0, 20.4, 10.4; Anal. Calcd. for $C_{20}N_2O_4 \cdot 0.37\ H_2O$. Theoretical: C, 66.90; H, 5.61; N, 7.80. Found: C, 66.90; H, 5.52; N, 7.75.

EXAMPLE 47

To 40 mL of stirred ethanol at 0° C. under nitrogen was slowly added thionyl chloride (3.3 mL, 45 mmol) followed by addition of 3-amino-3-(3-pyridyl)propionic acid (2.65 g, 15 mmol). The reaction mixture was allowed to slowly warm to room temperature and then refluxed for 3 hours. After 2 hours at reflux all of the solid had dissolved. The reaction mixture was allowed to cool to room temperature and stirred overnight. The slurry was filtered and the solid was washed with copious amounts of ethanol. The solid was dried in vacuo (60° C., <1 mm) to afford 3.17 g (79%) of ethyl 3-amino-3-(3-pyridyl)propionate hydrochloride as a white powder: 1H NMR (DMSO-$d_6$, 250 MHz) δ9.32 (br s, 3H), 9.21 (br s, 1H), 8.87–8.95 (m, 2H), 8.09–8.14 (m, 1H), 4.93 (br s, 1H), 3.90–4.15 (m, 2H), 3.20–3.38 (m, 2H), 1.11 (t, 3H, J=7 Hz); 13C NMR (DMSO-$d_6$) δ168.8, 144.5, 142.8, 142.6, 136.2, 126.7, 60.7, 47.9, 37.2, 13.9.

EXAMPLE 48

By following the procedure of Example 30 but utilizing ethyl 3-amino-3-(3-pyridyl)propionate hydrochloride, there is obtained ethyl 3-phthalimido-3-(3-pyridyl)propionate as a white powder (0.43 g, 71%): mp 72.3°–72.8° C.; 1H NMR (DMSO-$d_6$, 250 MHz) δ8.45–8.70 (m, 2H), 7.80–8.00 (m, 5H), 7.35–7.45 (m, 1H), 5.78 (dd, 1H, J1=6.5 Hz, J2=9.5 Hz), 4.01 (q, 2H, J=7 Hz), 3.62 (dd, 1H, J1=6.5 Hz, J2=16.4 Hz), 3.41 (dd, 1H, J1=9.5 Hz, J2=16.4 Hz), 1.05 (t, 3H, J=7 Hz); 13C NMR (DMSO-$d_6$) δ169.9, 167.5, 148.96, 148.4, 134.9, 134.7, 134.0, 131.0, 123,6, 123.3, 60.3, 47.9, 35.2, 13.8; Anal. Calcd. for C18H16N2O4. Theoretical: C, 66.66; H, 4.97; N, 8.64. Found: C, 66.51; H, 4.94; N, 8.56.

EXAMPLE 49

By following the procedure of Example 45 but utilizing 3-amino-3-(3,4-dimethoxyphenyl)propionic acid, 3-phthalimido-3-(3,4-dimethoxyphenyl)propionic acid was isolated as a white powder (5.30 g, 75%): 1H NMR (DMSO-$d_6$, 250 MHz) δ12.44 (br s, 1H), 7.70–8.00 (m, 4H), 6.85–7.10 (m, 3H), 5.63 (dd, 1H, J1=7 Hz, J2=9 Hz), 3.74 (s, 3H), 3.73 (s, 3H), 3.53 (dd, 1H, J1=9 Hz, J2=16.5 Hz), 3.26 (dd, 1H, J1=7 Hz, J2=16.5 Hz), 13C NMR (DMSO-$d_6$) δ171.8, 167.7, 148.6, 148.4, 134.7, 131.3, 131.1, 123.2, 119.3, 111.7, 111.0, 55.48, 55.46, 50.1, 36.1.

EXAMPLE 50

By following the procedure of Example 46 but utilizing 3-phthalimido-3-(3,4-dimethoxyphenyl)propionic acid, 3-phthalimido-3-(3,4-dimethoxyphenyl)propionamide was isolated as a white powder (0.314 g, 52%): mp 188.8°–190.0° C.; 1H NMR (DMSO-$d_6$, 250 MHz) δ7.7–8.0 (m, 4H), 7.54 (br s, 1H), 6.7–7.1 (m, 4H), 5.67 (t, 1H, J=8 Hz), 3.73 (s, 3H), 3.72(s, 3H), 3.20 (d, 2H, J=8 Hz); 13C NMR (DMSO-$d_6$) δ171.2. 167.7, 148.5, 134.7, 134.5, 131.7, 131.2; 123.1, 119.4, 111.6, 111.2, 55.5, 50.3, 37.0; Anal. Calcd. for $C_{19}H_{18}N_2O_5$. Theoretical: C, 64.40; H, 5.12; N, 7.91. Found: C, 64.01; H, 5.14; N, 7.64.

EXAMPLE 51

The procedure of Example 47 was followed starting with 3-amino-3-(3,4-dimethoxyphenyl)propionic acid except the reaction was run at room temperature. Ethyl 3-amino-3-(3, 4-dimethoxyphenyl)propionate was isolated as a white powder (2.04 g, 88%): 1H NMR (DMSO-$d_6$, 250 MHz) δ8.75 (br s, 3H), 7.30–7.35 (m, 1H), 6.90–7.05 (m, 2H), 4.50 (dd, 1H, J1=6 Hz, J2=9 Hz), 3.90–4.10 (m, 2H), 3.77 (s, 3.77 (s, 3H), 3.75 (s, 3H), 3.19 (dd, 1H, J1=6 Hz, J2=16 Hz), 2.98 (dd, 1H, J1=9 Hz, J2=16 Hz), 1.10 (t, 3H, J=7 Hz); 13C NMR (DMSO-$d_6$) δ169.1, 149.0, 148.6, 128.9, 120.1, 111.4, 60.4, 55.6, 55.5, 50.9, 38.7, 13.9.

EXAMPLE 52

The procedure of Example 30 was followed utilizing ethyl 3-amino-3-(3,4-dimethoxyphenyl)propionate. The reaction mixture was concentrated and the residue was dissolved in 20 mL of ethyl acetate and washed with water (3×20 mL). The organic phase was dried over sodium sulfate and then concentrated to afford 0.31 g (40%) of ethyl 3-phthalimido-3-(3,4-dimethoxyphenyl)propionate as a yellow oil: 1H NMR (DMSO-$d_6$, 250 MHz) δ7.80–7.95 (m, 4H), 7.04 (s, 1H), 6.85–6.98 (m, 2H), 5.65 (dd, 1H, J1=6 Hz, J2=10 Hz), 4.00 (q, 2H, J=7 Hz), 3.74 (s, 3H), 3.73 (s, 3H), 3.60 (dd, 1H, J1=10 Hz, J2=16 Hz), 3.32 (dd, 1H, J1=6 Hz, J2=16 Hz), 1.05 (t, 3J=7 Hz). 13C NMR (DMSO-$d_6$) $\delta$170.2, 167.5, 148.58, 148.54, 134.7, 131.1, 130.9, 123.2, 119.2, 111.6, 111.0, 60.1, 55.5, 50.0, 35.9, 13.9; Anal. Calcd. for $C_{21}H_{21}NO_6$. Theoretical: C, 65.79; H, 5.52; N, 3.65. Found: C, 65.13; H, 5.73; N, 3.61.

EXAMPLE 53

By following the procedure of Example 46 utilizing 3-phthalimido-3-(3,4-dimethoxyphenyl)propionic acid and amylamine (1.0 equiv) there is obtained 2.15 g (84%) of crude product. The crude product was dissolved in 150 mL of ethyl acetate and then 50 mL of ether was added and the mixture stirred for 1 hour. The resulting slurry was filtered and the solid dried in vacuo to afford 1.28 g (50%) yield of 3-phthalimido-3-(3,4-dimethoxyphenyl)propionic amylamide as a white powder: mp 140.5°–142.1° C.; 1H NMR (DMSO-$_6$, 250 MHz), $\delta$8.05 (t, 1H, J=5 Hz), 7.85 (m, 4H), 7.03 (br s, 1H), 6.90 (m, 3H), 5.68 (t, 1H, J=8 Hz), 3.73 (s, 3H), 3.71 (s, 3H), 3.19 (d, 2H, J=8 Hz), 2.8–3.1 (m, 2H), 0.9–1.3 (m, 6H), 0.74 (m, 3H); 13C NMR (DMSO-$d_6$) $\delta$168.8, 167.7, 148.5, 148.3, 134.5, 131.5, 131.2, 123.1, 119.5, 111.6, 111.1, 55.4, 50.6, 38.2, 37.4, 28.7, 28.3, 21.7, 13.7; Anal. Calcd. for $C_{24}H_{28}N_2O_5$. Theoretical: C, 67.9; H, 6.65; N, 6.60. Found: C, 67.84; H, 6.70; N, 6.57.

EXAMPLE 54

By following the procedure of Example 46 utilizing 3-phthalimido-3-(3,4-dimethoxyphenyl)propionic acid and benzylamine (1.0 equiv) there is obtained 2.45 g (92%) of 3-phthalimido-3-(3,4-dimethoxyphenyl)propionic benzylamide as white powder: mp 208.4°–209.8° C.; 1H NMR (DMSO-$_6$, 250 MHz) $\delta$8.60 (t, 1H, J=6 Hz), 7.78–7.92 (m, 4H), 6.85–7.20 (m, 8H), 5.73 (t, 1H, J=8 Hz), 4.10–4.30 (m, 2H), 3.73 (s, 3H), 3.72 (s, 3H), 3.20–3.45 (m, 2H); 13C NMR (DMSO-$d_6$) $\delta$169.1, 167.7, 148.5, 148.3, 139.2, 134.5, 131.4, 131.2, 127.9, 126.7, 123.1, 119.5, 111.5, 111.2, 101.9, 55.4, 55.37, 50.6, 41.7, 37.4; Anal. Calcd. for $C_{26}H_{24}N_2O_5$. Theoretical: C, 70.26; H, 5.44; N, 6.30. Found: C, 70.12; H, 5.53; N, 6.25.

EXAMPLE 55

The procedure of Example 46 was followed utilizing 3-phthalimido-3-(3,4-dimethoxyphenyl)propionic acid and ethylamine (1.0 equiv). After the reaction mixture was concentrated, the residue was diluted with 20 mL of water and 1 mL of ether. The mixture was stirred for 1 hour to afford a slurry. The slurry was filtered and the solid dried in vacuo to afford 0.66 g (77%) of 3-phthalimido-3-(3,4-dimethoxyphenyl)propionic ethylamide compound as a white powder: mp 131.0°–132.5° C.; 1H NMR (DMSO-$_6$, 250 MHz) $\delta$8.08 (t, 1H, J=5 Hz), 7.78–7.95 (m, 4H), 7.03 (s, 1H), 6.85–7.00 (m, 2H), 5.69 (t, 1H, J=8 Hz), 3.74 (s, 3H), 3.72 (s, 3H), 3.18 (d, 2H, J=8 Hz), 2.98 (m, 2H), 0.88 (t, 3H, J=7 Hz); 13C (DMSO-$d_6$) $\delta$168.8, 167.7, 148.5, 148.2, 134.5, 131.6, 131.2, 123.1, 119.4, 111.6, 111.1, 55.5, 50.5, 37.3, 33.2, 14.5; Anal. Calcd. for $C_{21}H_{22}N_2O_5$. Theoretical: C, 65.96; H, 5.80; N, 7.33. Found: C, 65.85; H, 5.84; N, 7.24.

EXAMPLE 56

The procedure of Example 45 was followed utilizing 3-amino-3-(4-ethoxyphenyl)propionic acid. 3-Phthalimido-3-(4-ethoxyphenyl)propionic acid was isolated as a white powder (2.52 g, 74%): mp 169.2°–171.1° C.; 1HNMR (DMSO-$_6$, 250 MHz) $\delta$7.75–8.00 (m, 4H), 7.34 (d, 2H, J=8.7 Hz), 6.89 (d, 2H, J=8.7 Hz), 5.64 (overlapping dd, 1H), 3.98 (q, 2H, J=7 Hz), 3.48 (dd, 1H, J1=9 Hz, J2=16.5 Hz), 3.26 (dd, 1H, J1=7 Hz, J2=16.5 Hz), 1.30 (t, 3H, J=7 Hz); 13C NMR (DMSO-$d_6$) $\delta$171.8, 167.7, 158.0, 134.7, 131.1, 130.8, 128.4, 123.2, 114.4, 63.0, 49.7, 36.1, 14.6; Anal. Calcd. for $C_{19}H_{17}NO_5$. Theoretical: C, 67.25; H, 5.05; N, 4.13. Found: C, 67.05,H, 4.93; N, 4.17.

EXAMPLE 57

By following the procedure of Example 46 utilizing 3-phthalimido-3(4-ethoxyphenyl)propionic acid there is obtained 1.3 g (88%) of crude product. Recrystallization of the crude material from ethyl acetate afforded 0.28 g (20%) of 3-phthalimido-3-(4-ethoxyphenyl)propionamide as a white powder: mp 190.6°–191.2° C.; 1H NMR (DMSO-$_6$, 250 MHz) $\delta$7.75–7.95 (m, 4H), 7.54 (br s, 1H), 7.33 (d, 2H, J=8.6 Hz), 6.75–6.98 (m, 3 H), 5.69 (t, 1H, J=8 Hz), 3.98 (q, 2H, J=7 Hz), 3.19 (d, 2H, J=8 Hz), 1.30 (t, 3H, J=7 Hz); 13C NMR (DMSO-$_6$, 250 Mhz) $\delta$167.6, 154.1, 154.2, 130.9, 127.6, 124.7, 119.5, 110.6, 59.4, 46.3, 33.3, 11.0; Anal. Calcd. for $C_{19}H_{18}N_2O_4$ 0.37 $H_2O$. Theoretical: C, 66.14; H, 5.26;N, 8.12. Found: C, 66.14; H, 5.26; N, 7.81.

EXAMPLE 58

A stirred mixture 3-amino-3-phenylpropionic acid and cis-1,2-cyclohexanedicarboxylic anhydride in 10 mL of acetic acid under nitrogen was heated to reflux for 4 h and then allowed to cool to room temperature. The resulting mixture was concentrated to an orange yellow oil. This oil was crystallized from a 1/1 mixture of ethyl acetate/hexane to afford 1.77 g (58%) of 3-(cis-hexahydrophthalimido)-3-phenylpropionic acid as white crystals: $^1$H NMR (DMSO-$d_6$) $\delta$12.45 (br s, 1H, COOH), 7.33 (m, 5H, Ph), 5.48 (dd, 1H, J=6.3, 9.6, CH), 3.41 (dd, 1H, J=16.5, 9.6 Hz), 3.14 (dd, 1H, J=16.5, 6.3 Hz), 2.50 (m, 2H), 1.8–1.1 (m, 8H); $^{13}$C NMR (DMSO-$d_6$) $\delta$179.3, 179.2, 171.7, 138.7, 128.4, 127.5, 126.8, 50.1, 38.7, 38.6, 35.2, 23.0, 22.9, 21.1. Anal. Calcd for $C_{17}H_{19}NO_4$. Theory: C, 67.76; H, 6.36; N, 4.65. Found: C, 67.52; H, 6.20; N, 4.60.

EXAMPLE 59

A mixture of 3-(cis-hexahydrophthalimido)-3-phenylpropionic acid (0.903 g, 3.00 mmol) and carbonyldiimidazole (0.525 g, 3.75 mmol) in 13 mL of anhydrous tetrahydrofuran under nitrogen was stirred for 1 hour, then 0.25 mL of concentrated ammonium hydroxide was added to the reaction solution. After 20 minutes, the reaction mixture was concentrated in vacuo to an oil. The oil was diluted with 20 mL of water and the mixture extracted with ethyl acetate (20 mL). The organic layer was dried (sodium sulfate) and concentrated to afford an oil. The oil was then purified by flash chromatography (silica gel, 5/95 methanol/methylene chloride, $R_f$=0.3) to afford 210 mg of 3-(cis-hexahydrophthalimido)-3-phenylpropionamide as an oil which slowly crystallized to an ivory solid: $^1$H NMR (DMSO-$d_6$) d7.49 (s, 1H, NH), 7.4–7.2 (m, 5H, Ar), 6.90 (s, 1H, NH), 5.54 (t, 1H, J=7.8 Hz, CH), 3.09 (d, 2H, J=7.8 Hz, CH2), 2.95–2.80 (m, 2H, CH2), 1.8–1.1 (m, 8H); $^{13}$C NMR (DMSO-$d_6$) $\delta$179.6, 179.5, 171.5, 139.5, 128.6, 127.7, 127.2, 55.2, 50.6, 38.8, 36.5, 23.4, 23.3, 21.5.

EXAMPLE 60

A stirred mixture of 4-methylphthalic acid anhydride (1.62 g, 10.0 mmol) and 3-amino-3-phenylpropionic acid (1.65 g, 10.0 mmol) in 15 mL of acetic acid under nitrogen was heated to reflux for 6 hours. The resulting reaction solution was concentrated in vacuo to an oil which was crystallized from 20 mL of a 1/1 mixture of ethyl acetate/hexane to afford 1.69 g (55%) of 3-(4-methylphthalimido)-3-phenylpropionic acid as an off-white powder: $^1$H NMR (DMSO-$d_6$) $\delta$12.5 (br s, 1H, COOH), 7.85–7.55 (m, 3 H, Ar), 7.55–7.2 (m, 5H, Ar), 5.68 (dd, 1H, J=9, 7 Hz, CH), 3.51 (dd, 1H, J=9, 16.5 Hz), 3.29 (dd, 1H, J=9, 16.5 Hz), 2.47 (s, 3H, CH3). Anal. Calcd for $C_{18}H_{15}N_{1O4}$ Theory; C, 69.89,H, 4.89, N, 4.53. Found: C, 69.45,H, 4.93, N, 4.55. HPLC: 95%.

EXAMPLE 61

A stirred mixture of cis-5-norbonene-endo-2,3-dicarboxylic anhydride (1.64 g, 10.0 mmol) and 3-amino-3-phenylpropionic acid (1.65 g, 10.0 mmol) in 15 mL of acetic acid under nitrogen was heated to reflux for 6 hours. The resulting reaction solution was concentrated in vacuo to an oil which was crystallized from a 1/1 mixture of ethyl acetate/hexane to afford 2.03 g (65%) of 3-(cis-5-norbonene-endo-2,3-dicarboxylic imide)-3-phenylpropionic acid as a white powder: $^1$H NMR (DMSO-$d_6$) $\delta$12.41 (br s, 1H, COOH), 7.29 (m, 5H, Ph), 6.0–5.7 (m, 2H), 5.37 (t, 1H, J=7.7 Hz), 3.5–3.1 (m, 6H), 1.49 (m, 2H); $^{13}$CNMR (DMSO-$d_6$) $\delta$177.2, 177.1, 171.4, 138.3, 134.3, 134.0, 128.1, 127.5, 127.1, 51.4, 50.1, 44.8, 44.5, 44.4, 35.1. Anal. Calcd for $C_8H_{17}NO_4$. Theory: C, 69.44; H, 5.50; N, 4.50. Found: C, 69.10; H, 5.33; N, 4.43.

EXAMPLE 62

A stirred mixture of 2,3,4,5-tetrachlorophthalic acid anhydride (2.85 g, 10.0 mmol) and 3-amino-3-(4-methoxyphenyl)propionic acid (1.95 g, 10.0 mmol) in 25 mL of acetic acid under nitrogen was heated to reflux for 4.5 hours. A solid formed as the reaction mixture cooled. The resulting slurry was filtered and the solid dried in vacuo (60° C., <2 mm) to afford 4.24 g (92%) of 3-(2,3,4,5-tetrachlorophthalimido)-3-(4-methoxyphenyl)-propionic acid as an off-white solid contaminated with~1% acetic acid: mp 235.6°–238° C.; $^1$H NMR (DMSO-$d_6$) $\delta$12.44 (br s, 1H, COOH), 7.36 (d, J=8.7 Hz, 2H), 6.90 (d, 1H, J=8.7 Hz), 5.64 (m, 1H), 3.72 (s, 3H), 3.35 (m, 2H); $^{13}$C NMR (DMSO-$d_6$) $\delta$171.5, 163.0, 158.8, 138.4, 129.9, 128.6, 128.2, 127.6, 113.8, 55.0, 50.2, 35.6. Anal. Calcd for $C_{18}H_{11}NO_5Cl_4$. Theory: C, 46.68; H, 2.39;N, 3.02. Found: C, 46.58; H, 2.31; N, 2.91.

EXAMPLE 63

A stirred mixture of 4-nitrophthalic acid anhydride (1.93 g, 10.0 mmol) and 3-amino-3-(4-methoxyphenyl)propionic acid (1.95 g, 10.0 mmol) in 20 mL of acetic acid under nitrogen was heated to reflux for 4.5 hours. The reaction mixture was concentrated to an oil which was stirred in 18 mL of ethyl acetate overnight. The resulting slurry was filtered and the solid air-dried and then dried in vacuo (70° C., <2 mm, 2 h) to afford 2.52 g (68%) of the product as a pale yellow powder contaminated with acetic acid and ethyl acetate. The material was dried in vacuo overnight at 90° C. to afford a yellow glass which was slurried in 15 mL of ethyl acetate to afford after filtration and drying 1.72 g (46%) of 3-(4-nitrophthalimido)-3-(4-methoxyphenyl)propionic acid as a pale yellow powder contaminated with ethyl acetate: mp 90°–91.5° C.; $^1$H NMR (DMSO-$d_6$) $\delta$8 8.75–8.60 (m, 1H), 8.5 (m, 2H), 8.12 (d, J=8 Hz, 1H), 7.38 (d, 2H, J=8.7 Hz H, Ar), 6.90 (d, 2H, J=8.7 Hz, Ar), 5.75–5.6 (m, 1H, CHCO), 3.72 (s, 3H, OMe), 3.47 (dd, 1H, J=8, 16.6 Hz), 3.33 (dd, 1 h, J=7 Hz, 16.6 Hz);$^{13}$C NMR (DMSO-$d_6$) $\delta$8 171.6, 165.9, 165.7, 158.8, 151.5, 135.6, 132.4, 130.3, 129.8, 128.5, 124.7, 118.0, 113.9, 55.0, 50.2, 35.8.. Anal. Calcd for $C_{18}H_{14}N_2O_7$–1/3 EtOAc. Theory: C, 58.09; H, 4.20; N, 7.01. Found: C, 57.89; H, 4.29; N, 6.83.

EXAMPLE 64

The procedure of Example 48 was followed utilizing 3-amino-3-(2-naphthyl)propionic acid and N-carbethoxyphthalimide. There is obtained 1.43 g (83%) of crude product as an off-white powder. The crude product was purified by flash chromatography (silica gel, 4–4.5% methanol/methylene chloride) to afford 1.11 g of product as a white foam. The foam was slurried in 15 mL of ethanol to afford 1.03 g of 3-phthalimido-3-(2-naphthyl)propionic acid as a white powder contaminated with ethanol and methylene chloride: $^1$H NMR (DMSO-$d_6$)d); 12.56 (br s, 1H), 8.1–7.75 (m, 8H), 7.7–7.45 (m, 3H), 5.89 (m, 1H), 3.62 (dd, 1H, J=16.6, 9 Hz), 3.46 (dd, J=16.6, 6.8 Hz); $^{13}$C NMR (DMSO-$d_6$) $\delta$5 171.8, 167.7, 136.3, 134.6, 132.6, 132.2, 131.1, 128.3, 127.9, 127.3, 126.3, 126.2, 125.6, 125.1,123.2, 50.2, 35.8.

EXAMPLE 65

The procedure of Example 34 was followed utilizing 3-phthalimido-3-(2-napthyl)propionic acid and carbonyldiimidazole. The crude product is obtained as a white powder. 3-Phthalimido-3o(2-naphthyl)propionamide was recrystallized from 40 mL of ethyl acetate to afford 0.259 g (35%) of the product as fine white prisms: $^1$H NMR (DMSO-$d_6$) $\delta$8.15–7.75 (m, 8H, Ar), 7.75–7.4 (m, 4 h, Ar and CONH), 6.94 (br s, 1H, CONH), 5.93 (overlapping dd, 1H, CHN), 3.55–3.15 (m, 2H, $CH_2CO$); $^{13}$C NMR (DMSO-$d_6$) $\delta$171.2, 167.7, 136.7, 134.5, 132.6, 132.2, 131.2, 128.1,127.8, 127.3, 126.3, 126.1, 125.5, 125.2, 123.1, 50.4, 36.7. Anal. Calcd for $C_{21}H_{16}N_2O_3$. Theory: C, 73.24; H, 4.68; N, 8.13. Found: C, 73.07; H, 4.61; N, 7.91.

EXAMPLE 66

A stirred suspension of 3-amino-3-(3,4-dimethoxyphenyl) propionic acid hydrochloride (0.689 g, 2.50 mmol) and 4-pyridyldicarboxylic acid anhydride (0.373 g, 2.50 mmol) in 20 mL of acetic acid was refluxed for overnight. The cooled reaction was filtered to remove a trace amount of solid and the filtrate concentrated to a thick yellow oil. The oil was diluted with 20 mL of ethyl acetate and heated to reflux and allowed to cool to room temperature. The resulting slurry was filtered and the filtrate concentrated to afford a yellow oil which was purified by flash chromatography (silica gel, 2/8 ethyl acetate/methylene chloride) to afford 0.592 g (64%) of methyl 3-(1,3-dioxo-5-azaisoindol-2-yl)-3-(3,4-dimethoxyphenyl)-propionate as a yellow oil which slowly solidified to afford a very pale yellow solid: $^1$H NMR (DMSO-$d_6$) $\delta$8.15–7.75 (m, 8H, Ar), 7.75–7.4 (m, 4 h, Ar and CONH), 9.13 (s, 1H, Ar), 9.11 (d, 1H, J=4.8 Hz), 7.90 (d, 1H, J=4.8 Hz), 7.03 (s, 1H), 6.93 (m, 2H), 5.67 (overlapping dd, 1H), 3.74 (s, 3H), 3.73 (s, 3H), 3.56 (s, 3H), 3.65–3.30 (m, 2H); $^{13}$C NMR (DMSO-$d_6$) $\delta$170.7, 166.9, 166.5, 156.0, 148.6, 148.5, 144.1, 138.7, 130.4, 125.2, 119.1, 116.9, 111.6, 111.1, 55.4, 51.6, 50.1,35.4.

EXAMPLE 67

To a stirred solution of 3-amino-3-(4-benzyloxy-3-methoxyphenyl)propionic acid (1.505 g, 5.00 mmol) and sodium carbonate (0.572 g, 5.40 mmol) in a mixture of 75 mL of water and 175 mL of acetonitrile (mixture was warmed gently to dissolve solid) was added N-carbethoxyphthalimide (1.096 g, 5.00 mmol). The mixture was stirred for 1 hour, then partially concentrated in vacuo to remove the acetonitrile. A small amount of solid formed which was removed by filtration. The pH of the solution was adjusted to 1 with 4N Hydrochloric acid, a gum formed. To the stirred mixture was added 1 mL of ether and the mixture was then stirred overnight. The resulting slurry was filtered and the solid dried to afford 1.63 g (75%) of 3-phthalimido-3-(4-benzyloxy-3-methoxyphenyl)-propionic acid as a white powder, $^1$H NMR (DMSO-$d_6$) δ12.43 (br s, 1H, COOH), 8.0–7.8 (m, 4H, Ar), 7.60–7.25 (m, 5H), 7.15–6.85 (m, 3H, Ar), 5.25 (dd, 1H, J=9, 6.6 Hz), 5.05 (s, 2H, OCH2), 3.76 (s, 3H, OMe), 3.52 (dd, 1H, J=9, 16.5 Hz), 2.29 (dd, 1 H, J=6.6, 16.5 Hz); $^{13}$C NMR (DMSO-$d_6$) δ171.7, 167.6, 148.9, 147.3, 137.0, 134.6, 131.7, 131.0, 128.3, 127.7, 127.6, 123.1, 119.1, 113.3, 111.3, 69.8, 55.5, 50.1, 36.0. Anal. Calcd for $C_{25}H_{21}N_1O_6$. Theory: C, 69.66; H, 4.91; N, 3.25. Found: C, 69.50; H, 4.85; N, 3.22.

EXAMPLE 68

A mixture of 3-phthalimido-3-(4-benzyloxy-3-methoxyphenyl)propionic acid (1.00 g, 2.32 mmol), carbonyldiimidazole (0.406 g, 2.50 mmol) and a catalytic amount of di-methylaminopyridine in 20 mL of dry tetrahydrofuran under nitrogen was stirred for 1 hour. To the reaction solution was then added 0.25 mL of concentrated ammonium hydroxide. After 15 minutes, the reaction mixture was concentrated in vacuo to an oil which was diluted with 20 mL of water and stirred overnight. The resulting slurry was filtered and the solid dried to afford 0.645 g (65%) of 3-phthalimido-3-(4-benzyloxy-3-methoxyphenyl)propionamide as a white powder: $^1$H NMR (DMSO-$d_6$) δ7.84 (m, 4H, Ar), 7.60–7.25 (m, 5H), 7.53 (br s, 1H, CONH), 7.15–6.8 (m, 4H), 5.67 (t, 1H, J=7.8 Hz), 5.04 (s, 2H, OCH2), 3.75 (s, 3H, OMe), 3.19 (d, 2H, J=9, 16.5 Hz); $^{13}$C NMR (DMSO-$d_6$) δ171.1, 167.6, 148.8, 147.2, 137.0, 134.5, 132.0, 131.2, 128.3, 127.7, 127.6, 123.0, 119.3, 113.2, 111.4, 69.8, 55.5, 50.3, 36.9. Anal. Calcd for $C_{25}H_{22}N_2O_5$. Theory C, 69.76; H, 5.15; N, 6.51. Found: C, 69.54; H, 5.13; N, 6.28.

EXAMPLE 69

To a stirred solution of 3-amino-3-(4-butoxy-3-methoxyphenyl)propionic acid (1.31 g, 4.98 mmol) and sodium carbonate (0.554 g, 5.23 mmol) in a mixture of 100 mL of water and 100 mL of acetonitrile (mixture was warmed gently to dissolve solid, small amount of brown solid did not dissolve removed by filtration) was added N-carbethoxyphthalimide (1.09 g, 4.98 mmol). The mixture was stirred for 1 hour, then partially concentrated in vacuo to remove the acetonitrile. The pH was adjusted to 0–1 with 4N Hydrochloric acid. An oil formed, 3 mL of ether was added and the mixture stirred overnight The oil did not solidify and was extracted in methylene chloride. The organic layer was dried (sodium sulfate) and concentrated to a yellow oil which was purified by flash chromatography (silica gel, 5/95 methanol/methylene chloride) to afford 1.02 g of 3-phthalimido-3-(4-butoxy-3-methoxyphenyl) propionic acid containing an unidentified impurity as a yellow oil which slowly crystallized: $^1$H NMR (DMSO-$d_6$) δ7.95–7.8 (m, 4H, Ar), 7.03 (s, 1H), 6.9 (m, 2H), 5.61 (dd, 1H, J=9, 6.7 Hz), 3.91 (t, 2H, J=6.4 Hz), 3.74 (s, 3H), 3.47 (dd, 1H, J=16.5, 6.7 Hz), 3.27 (dd, 1H, J=16.5, 6.7 Hz), 1.75–1.55 (m, 2H) 1.5–1.3 (m, 2H), 0.91 (t, 3H, J=7.3 Hz); $^{13}$C NMR (DMSO-$d_6$) δ171.8, 167.7, 148.8, 147.8, 134.6, 131.3, 131.1, 123.2, 119.3, 112.9, 111.4, 67.8, 55.5, 50.1, 30.8, 18.7, 13.6.

EXAMPLE 70

By following the procedure of Example 65 utilizing 3-phthalimido-3-(4-butoxy-3-methoxyphenyl)propionic acid and carbonyldiimidazole, there is obtained 0.742 g (74%) of crude product as a pale yellow powder. The crude product was recrystallized from ethyl acetate (16 mL) to afford 0.517 (52%) of 3-phthalimido-3-(4-butoxy-3-methoxyphenyl)propionamide as fine fluffy white needles: HPLC 99.1%; $^1$H NMR (DMSO-$d_6$) δ7.95–7.75 (m, 4H, Ar), 7.54 (br s, 1H, CONH), 7.04 (s, 1H, Ar), 7.0–6.75 (m, 2H), 6.86 (br s, 1H, CONH), 5.67 (t, 1H, J=8 Hz), 3.90 (t, 2H, J=6 Hz), 3.73 (s, 3H), 3.20 (d, 1H, J=8 Hz, CH$_2$CO), 1.8–1.55 (m, 2H) 1.5–1.3 (m, 2H), 0.91 (t, 3H, J=7 Hz); $^{13}$C NMR (DMSO-$d_6$) δ171.2, 167.6, 148.8, 147.7, 134.5, 131.6, 131.2, 123.0, 119.4, 112.8, 111.4, 67.8, 55.5, 50.3, 36.9, 30.7, 18.6, 13.6.

EXAMPLE 71

A stirred mixture of tetrachlorophthalic anhydride (2.85 g, 10.0 mmol) and phenylglycine (10.0 mmol) in 20 mL of acetic acid under nitrogen was heated to reflux for 4 hours. The reaction solution was allowed to cool to room temperature with stirring. The resulting slurry was filtered and the solid dried to afford 3.58 g (85%) of α-(3,4,5,6-tetrachlorophthalimidio)phenylacetic acid as a white powder: $^1$H NMR (DMSO-$d_6$) δ7.55–7.25 (m, 5H, Ph), 6.06 (s, 1H, CH); $^{13}$C NMR (DMSO-$d_6$) δ168.4, 162.5, 138.8, 134.2, 129.4, 128.6, 128.1, 128.1, 127.6, 55.7. Anal. Calcd for $C_{16}H_7N_1O_4Cl_4$. Theory: C, 45.68; H, 1.68; N, 3.34. Found: C, 45.78; H, 1.61; N, 3.29.

EXAMPLE 72

A mixture of 4,5-dichlorophthalic anhydride (2.17 g, 10.0 mmol) and D,L-phenylglycine (Aldrich, 95%) (1.59 g, 10.0 mmol) in 20 mL of acetic acid was refluxed for 6 h under nitrogen. The reaction mixture was allowed to cool. The slurry was filtered and the solid was dried to afford 2.86 g (82%) of α-(4,5-dichlorophthalimido)phenylacetic acid as a white powder: mp 228°–232° C.; $^1$H NMR (DMSO-$d_6$, 250 MHz) d: 8.25 (s, 8H), 7.52–7.30 (m, 5H), 6.04 (s, 1H); $^{13}$C NMR (DMSO-$d_6$) δ168.7, 165.2, 138.0, 134.6, 130.9, 129.3, 128.1, 128.1, 125.8, 55.5. Anal. Calcd for $C_{16}H_9NO4Cl_2$. Theoretical: C, 54.88; H, 2.59; N, 4.00. Found: C, 54.93; H, 2.54; N, 3.95.

EXAMPLE 73

A slurry of 3-nitrophthalic anhydride (1.93 g, 10.0 mmol) and D,L-phenylglycine (Aldrich, 95%) (1.59 g, 10.0 mmol) in 20 mL of acetic acid was refluxed for 5 h under nitrogen. The mixture was cooled, the slurry filtered and the solid dried to afford 2.32 g (72%) of α-(3-nitrophthalimido) phenylacetic acid as a white powder. mp 213°–229° C.; 1H NMR (DMSO-$_6$, 250 MHz) δ8.40–8.02 (m, 3H), 7.55–7.26 (m, 5H), 6.08 (s, 1H); $^{13}$C NMR (DMSO-$d_6$) δ168.6, 165.1, 162.4, 144.5, 136.8, 134.4, 132.8, 129.4, 129.0, 128.1, 128.1, 127.5, 122.5, 55.6. Anal. Calcd for $C_{16}H_{10}N_2O_4$. Theoretical: C, 65.31; H,3.43; N, 9.52. Found: C, 58.89; H, 3.11; N, 8.52.

EXAMPLE 74

A mixture of 3-nitrophthalic anhydride (1.54 g, 8.0 mmol) and 3-amino-3-(4-methoxyphenyl)propionic acid (1.56 g, 8.0 mmol) in 15 mL of acetic acid was refluxed for 3.5 h under nitrogen. The reaction was cooled and removed some of the solvent. The slurry was filtered and the solid was dried to afford 2.34 g (79%) of 3-(4-methoxyphenyl)-3-(3-nitrophthalimido)propionic acid as a white powder: mp 178°–180° C.; $^1$H NMR (DMSO-$_6$, 250 MHz) δ8.07–8.02 (m, 3H), 7.38 (d, 2H, J=8.7), 6.90 (d, 2H, J=8.7, 5.68–5.07 (m, 1H), 3.72 (s, 3H), 3.48–3.22 (m, 2H); $^{13}$C NMR (DMSO-d$_6$) δ171.6, 165.7, 163.0, 158.8, 144.4, 136.4, 133.0, 130.2, 128.6, 128.5, 127.0, 122.4, 113.9, 55.1, 50.0, 35.8. Anal. Calcd for $C_{18}H_{14}N_2O_7$. Theoretical: C, 58.38; H,3.81; N, 7.56. Found: C, 58.18; H, 3.79; N, 7.36.

EXAMPLE 75

A mixture of 4.5-dichlorophthalic anhydride (0.91, 4.19 mmol) and 3-amino-3-(4-methoxyphenyl)propionic acid in 10 mL acetic acid was stirred under nitrogen for 6 hours. The reaction was cooled and removed some of the solvent. The slurry was filtered and the solid was dried to afford 1.20 g (61%) of 3-(4,5-dichlorophthalimido)-3-(4-methoxyphenyl) propionic acid as a white powder. mp 182°–185° C; $^1$H NMR (DMSO-$_6$, 250 MHz) δ8.19(s, 2H), 7.34 (d, 2H, J=8.7), 6.90 (d, 2H, J=8.7), 5.61 (t, 1H, J=7.8), 3.72 (s, 3H), 3.50–3.20 (m, 2H). $^{13}$C NMR (DMSO-d$_6$) δ171.6, 165.8, 158.8, 137.6, 131.0, 130.4, 128.4, 125.4, 113.9, 55.1, 50.0, 35.8. Anal. Calcd for $C_{18}H_{14}N_2O_7$. Theoretical: pending

EXAMPLE 76

A mixture of 3-phthalimido-3-(3,4-dimethoxyphenyl) propionic acid (0.86 g, 2.41 mmol) and carbonyldiimidazole (0.43 g, 2.65 mmol) with trace amount of 4-dimethylaminopyridine in 10 mL of tetrahydrofuran under nitrogen was stirred for 30 in at room temperature, then 0.23 mL (2.41 mmol) of 3-pyridylcarbinol was added to the above solution After 1 hour, the reaction mixture was concentrated to an oil. The oil was dissolved in 25 mL of ethylacetate and the mixture was extracted with water (3×25 mL). The organic layer was dried over sodium sulfate and to afford the crude product as a light yellow. The crude product was then purified by flash chromatography (silica gel, methanol/methylene chloride, 0–2%, (v/v)) to afford 0.54 g (50%) of 3-pyridinemethyl 3-phthalimido- 3-(3,4-dimethoxyphenyl) propionate as a light yellow foam: $^1$H NMR (DMSO-$_6$, 250 MHz) δ8.4–8.5 (m, 2H), 7.84 (s, 4H, Ar), 7.5–7.6 (m, 1H), 7.2–7.3 (m, 1H), 6.7–7.1 (m, 3H, Ar), 5.65 (dd, 1H, J$_1$=6 Hz, J$_2$=9.6 Hz), 5.09 (s, 2H), 3.74 (s, 6H), 3.4–3.7 (m, 2H); $^{13}$C NMR (DMSO-d$_6$)$_δ$170.1, 167.6, 149.2, 148.6, 148.4, 135.7, 134.7, 131.4, 131.0, 130.8, 123.3, 123.2, 119.3, 111.7, 111.0, 63.4, 55.5, 55.4, 49.9, 35.9. Anal. Calcd for $C_{25}H_{22}N_2O_6$. Theoretical C, 67.26; H, 4.97; N, 6.27. Found C, 67.06; H, 4.99; N, 6.20.

EXAMPLE 77

A mixture of 3-phthalimido-3-(3,4-dimethoxyphenyl) propionic acid (0.60 g, 1.69 mmol), carbonyldiimidazole (0.28 g, 1.77 mmol) and a trace amount of 4-dimethylaminopyridine in 10 mL of tetrahydrofuran was stirred at room temperature under nitrogen for 30 min. To the reaction mixture was added 3-aminomethylpyridine (0.18 mL, 1.77 mmol). The reaction mixture was stirred for 20 min, then 10 mL of water was added and the tetrahydrofuran was removed under reduced pressure. The resulting slurry was filtered the solid was washed with water, and dried in vacuo (60° C., <1 mm) to afford 0.57 g (76%) of N-3-methylpyridyl 3-phthalimido-3-(3,4-dimethoxyphenyl) propionamide as a white powder: mp 171.2°–172.4° C.; $^1$H NMR (DMSO-$_6$, 250 MHz) δ8.69 (t, 1H, J=6 Hz), 8.36 (m, 2H), 7.85 (s, 4H, Ar), 6.8–7.4 (m, 5H), 5.71 (t, 1H, J=8 Hz), 4.22 (d, 2H, J=5.2 Hz), 3.73 (s, 3H), 3.71 (s, 3H), 3.31 (d, 2H, J=8 Hz); $^{13}$C NMR (DMSO-d$_6$) δ169.4, 167.7, 148.5, 148.3, 147.9, 134.7, 134.6, 134.5, 131.4, 131.2, 123.1, 119.5, 111.6, 111.2, 55.5, 55.4, 50.6, 39.6, 37.4. Anal. Calcd for $C_{25}H_{23}N_3O_5$. Theoretical C, 67.41; H, 5.20; N, 9.43. Found C, 67.35; H, 5.14; N, 9.34.

EXAMPLE 78

To a stirred solution of 3-phthalimido-3-(3,4-dichlorophenyl)propionic acid (1.10 g, 3.02 mmol) in 20 mL of tetrahydrofuran at room temperature under nitrogen was added carbonyldiimidazole (0.51 g, 3.17 mmol) and a catalytic amount of 4-dimethylaminopyridine The mixture was stirred for 45 in and then concentrated ammonium hydroxide (0.21 mL, 3.2 mmol) was added. The reaction mixture was stirred for 10 minutes and then the tetrahydrofuran was removed under reduced pressure. To the resulting mixture was added 20 mL of water, a light yellow oil was formed. To the mixture was added 3 mL of ether, the mixture was stirred at room temperature for 1 hour. The resulting slurry was filtered, the solid was washed with water and air-dried to afford 0.73 g of the crude product as a white solid. The crude product was purified by flash chromatography (silica gel, hexane/methylene chloride, 220% (v/v)) to afford 0.39 g (36%) of 3-phthalimido-3-(3,4-dichlorophenyl) propionamide as a white powder: $^1$H NMR (DMSO-d$_6$, 250 MHz) δ7.83 (m, 4H, Ar), 7.35–7.75 (m, 4H), 6.93 (br s, 1H), 5.72 (t, 1H, J=8 Hz), 3.23 (dd, 1H, J$_1$=8 Hz, J$_2$=15 Hz), 3.14 (dd, 1H, J$_1$=8 Hz, J$_2$=15 Hz); $^{13}$C NMR (DMSO-d$_6$) δ170.8, 167.6, 140.2, 134.6, 131.2, 131.0, 130.7, 130.3, 129.2, 127.7, 123.2, 49.3, 36.5. Anal. Calcd for $C_{17}H_{12}N_2O_3Cl_2$. Theoretical C, 54.69; H, 3.54; N, 7.53. Found C, 54.69; H, 3.38; N, 7.15.

EXAMPLE 79

To 150 mL of stirred methanol at 0° C. under nitrogen was slowly added thionyl chloride (14.2 mL, 194.4 mmol). To the reaction mixture was then added 3-amino-3-(3,4-dimethoxyphenyl)propionic acid (15.5 g, 64.8 mmol). The reaction mixture was stirred at 0° C. for 30 minutes and then allowed to warm to room temperature, and stirred overnight. The reaction solution was concentrated to an oil and then diluted with 200 mL of CH$_3$OH/Et$_2$O (1/3) and stirred. The resulting slurry was filtered and the solid was washed with a copious amount of ether. The solid was dried in vacuo (60° C., <1 mm) to afford 1.83 g (66%) of methyl 3-amino-3-(3, 4-dimethoxyphenyl)propionate hydrochloride as a white powder: $^1$H NMR (DMSO-$_6$, 250 MHz) δ8.59 (br s, 3H, NH$_3$), 6.9–7.3 (m, 3H, Ar), 4.52 (overlapping dd, 1H), 3.77 (s, 3H, OCH$_3$), 3.75 (s, 3H, OCH$_3$), 3.67 (s, 3H, OCH$_3$), 3.16 (dd, 1H, J$_1$=6 Hz, J$_2$=16 Hz), 2.98 (dd, 1H, J$_1$=8 Hz. J$_2$=16 Hz); $^{13}$C NMR (DMSO-d$_6$) δ169.6, 149.0, 129.0, 120.0, 111.5, 111.4, 55.7, 55.5, 51.7, 50.8, 38.5. Anal. Calcd for $C_{12}H_{18}NO_4Cl$. Theoretical C, 52.27; H, 6.58; N, 5.08. Found C, 52.44; H, 6.53; N, 5.01.

EXAMPLE 80

A mixture of methyl 3-amino-3-(3,4-dimethoxyphenyl) propionate hydrochloride (1.38 g, 5.00 mmol), sodium carbonate (0.53 g, 5.00 mmol), and N-carbethoxyphthalimide (1.10 g, 5.0 mmol) in 40 mL of acetonitrile/water (1/1) was stirred for 1 hour at room temperature. The reaction solution was then partially concentrated under reduced pressure to remove the acetonitrile. This afforded a white gum in water.

To the mixture was then added 5 mL of ether and the mixture was stirred for 2 hours. The resulting slurry was filtered, the solid was washed with a copious amount of water and air-dried overnight to afford 1.69 g (92%) of methyl 3-phthalimido-3-(3,4-dimethoxyphenyl)propionate as a white solid: mp 114.1°–115.6° C.; $^1$H NMR (DMSO-d$_6$, 250 MHz)d 7.80–7.95 (m, 4H, Ar), 6.80–7.10 (m, 3H, Ar), 5.65 (dd, 1H, J$_1$=7 Hz, J$_2$=9 Hz), 3.74 (s, 3.74 H, OCH$_3$), 3.72 (s, 3H, OCH$_3$), 3.55 (s, 3H, OCH$_3$), 3.30–3.67 (m, 2H); $^{13}$C NMR d(DMSO-d$_6$)d 170.8, 167.6, 148.6, 148.4, 134.7, 131.1, 131.0, 123.2, 119.3, 111.7, 111.0, 55.5, 51.6, 49.9, 35.6. Anal. Calcd for C$_{20}$H$_{19}$NO$_6$. Theoretical C, 65.03; H, 5.18; N, 3.79. Found C, 65.17; H, 5.14; N, 3.75. HPLC 99%.

EXAMPLE 81

To a stirred solution of benzaldehyde (1.58 mL, 15.5 mmol) in 10 mL of absolute ethanol at room temperature under nitrogen was added (R)-α-methylbenzylamine (2.0 mL, 15.51 mmol, 99% ee.). The reaction mixture was stirred for 3 hours. The reaction solution was then dried over magnesium sulfate and diluted to a 60 mL volume with EtOH. Ethanol washed Raney nickel Ni (~1.5 g) was added and the resulting suspension was treated with 58 psi of hydrogen in a Parr Type Shaker. After 1 day, additional Raney nickel (~1 g) and 30 mL of ethanol were added and the hydrogenolysis continued for 3 days. The reaction mixture was filtered through Celite to remove the catalyst and concentrated to afford 3.11 g (95%) of N-benzyl (R)-α-methylbenzylamine as a pale yellow oil contaminated with~5% of benzyl alcohol and (R)-α-methylbenzylamine; $^1$H NMR (DMSO-$_6$, 250 MHz) δ7.1–7.5 (m, 10H, Ar), 3.68 (q, 1H, J=6.6 Hz), 3.48 (dd, 2H, J$_1$=13.6 Hz, J$_2$=20.5 Hz), 1.26 (d, 3H, J=6.6 Hz, CH$_3$); $^{13}$C NMR (DMSO-d$_6$) δ146.1, 141.0, 128.2, 128.0, 127.8, 126.5, 126.4, 56.7, 50.6, 24.5. This mixture was used directly in the next reaction.

EXAMPLE 82

To stirred solution of N-benzyl (R)-α-methylbenzylamine (1.9 g, 9.0 mmol) in 50 mL of tetrahydrofuran at 0° C. under nitrogen was added n-butyl lithium (1.6M in hexanes; 9.0 mmol). The resulting red solution was stirred at 0° C. for 15 min and then cooled to −78° C. To the reaction mixture was then dropwise added methyl trans-3-(3,4-dimethoxyphenyl)propion-2-enate (1.33 g, 6.0 mmol) in 20 mL tetrahydrofuran and the mixture was stirred for 15 in at −78° C. to afford a yellow solution. The reaction was then quenched by the addition of saturated ammonium chloride (20 mL). The mixture was allowed to warm to room temperature and poured into 40 mL of saturated sodium chloride (aq). The mixture was extracted with ether (2×60 mL) and the combined organic layers dried (MgSO$_4$) and concentrated to afford 3.35 g of crude product as a yellow oil. The oil was purified by flash chromatography (silica gel, hexane/methylene chloride, 30–0%, (v/v)) to afford 1.24 g (48%) of methyl (S)-N-benzyl-N-(R)-α-methylbenzyl-3-(3,4-dimethoxyphenyl)propionate adduct as colorless oil: $^1$H NMR (DMSO-$_6$, 250 MHz) δ6.7–7.5 (m, 13H, Ar), 3.9–4.2 (m, 2H), 3.78 (s, 3H, OCH$_3$), 3.73 (s, 3H, OCH$_3$), 3.65 (s, 2H), 3.43 (s, 3H, OCH$_3$), 2.6–2.9 (m, 2H), 1.03 (d, 3H, J=7 Hz); $^{13}$C NMR (DMSO-d$_6$) δ171.6, 148.3, 147.8, 144.6, 141.5, 133.6, 128.1, 128.0, 127.7, 127.5, 126.7, 126.4, 119.6, 111.9, 111.2, 58.2, 56.4, 55.4, 55.3, 51.1, 49.7, 35.6, 17.1.

EXAMPLE 83

Debenzylation of the above pure adduct of Example 82 was performed following the procedure S. G. Davies and O. Ichihara (*Tetrahedron Asymmetry* 1991, 2, 183.). To a stirred solution methyl (S)-3-(N-benzyl-N-(R)-α-methylbenzylamino)-3-(3,4-dimethoxyphenyl)propionate (1.20 g, 2.77 mmol) in a mixture of methanol (20 mL), water (2 mL) and acetic acid (0.5 mL) was added 20% palladium hydroxide on charcoal. The reaction mixture was treated with hydrogen (54 psi) at room temperature for 23 h on a Parr Type Shaker. The reaction mixture was filtered through Celite and then concentrated to afford the product as an acetate salt. The salt was dissolved in 10 mL of water, stirred with 0.7 mL 4N HCl and then concentrated to a white solid. The solid was diluted with 40 mL of ether and stirred for 20 min. The slurry was filtered and the solid was dried in vacuo (room temperature, <1 mm) to afford 0.57 g (75%) of methyl (S)-3-amino-3-(3,4-dimethoxyphenyl)propionate hydrochloride as a white solid: HPLC 96% ee (Chiral Crown-pack CR+ column); $^1$H NMR (DMSO-$_6$, 250 MHz) δ8.73 (br s, 3H, NH$_3$), 6.90–7.40 (m, 3H, Ar), 4.51 (dd, 1H, J$_1$=6 Hz, J$_2$=8 Hz), 3.77 (s, 3H, OCH$_3$), 3.75 (s, 3H, OCH$_3$), 3.56 (s, 3H, OCH$_3$), 3.2 (dd, 1H, J$_1$=6 Hz, J$_2$=16 Hz), 3.0 (dd, 1H, J$_1$=8 Hz, J$_2$=16 Hz); $^{13}$C NMR (DMSO-d$_6$) δ169.6, 149.0, 148.7, 129.0, 120.0, 111.5, 111.4, 55.7, 55.5, 51.7, 50.8, 38.6. Anal. Calcd for C$_{12}$H$_{18}$NO4Cl-0.48 H$_2$O. Theoretical C, 50.67; H, 6.72; N, 4.92. Found C, 50.67; H, 6.46; N, 4.83.

EXAMPLE 84

Methyl (S)-3-amino-3-(3,4-dimethoxyphenyl)propionate (0.45 g, 1.63 mmol), sodium carbonate (0.17 g, 1.63 mmol) and N-carboethoxyphthalimide (0.36 g, 1.63 mmol) were allowed to react according to the procedure of Example 85. Methyl (S)-3-phthalimido-3-(3,4-dimethoxyphenyl) propionate was obtained as a white powder, 0.51 g (85%); $^1$H NMR (DMSO-$_6$, 250 MHz) δ7.87 (br s, 4H, Ar), 6.80–7.10 (m, 3H, Ar), 5.65 (dd, 1H, J$_1$=7 Hz, J$_2$=9 Hz), 3.73 (s, 3H, OCH$_3$), 3.72 (s, 3H, OCH$_3$), 3.55 (s 3H, OCH$_3$), 3.30–3.67 (m, 2H); $^{13}$C NMR (DMSO-d$_6$) δ170.8, 167.7, 148.6, 148.4, 134.7, 131.1, 131.0, 123.2, 119.3, 111.7, 111.0, 55.5, 51.6, 49.9, 35.6. Anal. Calcd for C$_{20}$H$_{19}$NO$_6$. Theoretical C, 65.03; H, 5.18; N, 3.79. Found C, 64.94; H, 5.29; N, 3.86. HPLC 97%.

EXAMPLE 85

Benzaldehyde (3.94 mL, 38.8 mmol) and (S)-α-methylbenzylamine (5.0 mL, 38.8 mmol, 96% ee.) were allowed to react according to the procedure of Example 86 to yield 7.88 g (96%) of N-benzyl-(S)-α-methylbenzylamine as an oil contaminated with ~5% of benzyl alcohol and (S)-α-methylbenzylamine: $^1$H NMR (DMSO-$_6$, 250 MHz) δ7.15–7.45 (m, 10H, Ar), 3.69 (q, 1H, J=6.5 Hz), 3.48 (dd, 2H, J$_1$=13.6 Hz, J$_2$=20.9 Hz), 2.45 (br s, 1H, NH), 1.26 (d, 3H, J=6.5 Hz, CH$_3$); $^{13}$C NMR (DMSO-d$_6$) δ146.0, 141.0, 128.1, 128.0, 127.8, 126.4, 126.3, 56.7, 50.6, 24.5. This mixture was directly used in the next reaction.

EXAMPLE 86

Butyl lithium (1.6M in hexanes; 8.44 mmol), N-benzyl-(S)-α-methylbenylamine (1.78 g, 8.44 mmol) and 3-(3,4-dimethoxyphenyl)propyl-2-enate (1.50 g, 6.75 mmol) were allowed to react according to the procedure of Example 87 to yield 3.7 g of the crude product as a yellow oil. The oil was purified by flash chromatography (silica gel, ether/hexane, 20/80) to afford 0.57 g (20%) of methyl (R)-3-(N-benzyl-N-(S)-α-methylbenzylamino)-3-(3,4-dimethoxyphenyl)propionate as a colorless oil; $^1$H NMR (DMSO-$_6$, 250 MHz) δ6.80–7.50 (m, 13H, Ar), 4.15 (dd, 1H, J₁=6 Hz, J₂=9 Hz), 4.04 (q, 1H, J=7 Hz), 3.78 (s, 3H, OCH₃), 3.73 (s, 3H, OCH₃), 3.69 (s, 2H), 3.43 (s, 3H, OCH₃), 2.87 (dd, 1H, J₁=6 Hz, J₂=15 Hz), 2.67 (dd, 1H, J₁=9 Hz, J₂=15 Hz), 1.04 (d, 3H, J=7 Hz, CH₃); $^{13}$C NMR (DMSO-d₆) δ171.6, 148.4, 147.8, 144.7, 141.5, 133.6, 128.1, 128.0, 127.8, 127.5, 126.7, 126.4, 119.6, 111.9, 111.2, 58.2, 56.4, 55.4, 55.3, 51.1, 49.7, 35.6, 17.1.

EXAMPLE 87

Debenzylation of the adduct prepared in Example 86 was performed as described in Example 88. A solution of methyl (R)-3-(N-benzyl-N-(S)-α-methylbenzylamino)-3-( 3,4-dimethoxyphenyl)propionate (0.57 g, 1.3 mmol) in methanol (10 mL), water (1 mL) and acetic acid (0.25 mL) in the presence of 20% palladium hydroxide on charcoal was treated with hydrogen (59 psi) at room temperature for 23 h in a Parr Type Shaker. The mixture was filtered through Celite and then concentrated to afford the primary amine in an acetate salt, which was dissolved in 10 mL of water, stirred with 0.32 mL (4N) HCl and concentrated to a white solid. To the solid was added 10 mL of ether and the mixture stirred for 30 min. The slurry was filtered, the solid was dried in vacuo (room temperature <1 mm) to afford 0.32 g (90%) of methyl (R)-3-amino-3-(3,4-dimethoxyphenyl)propionate hydrochloride as a white powder: Chiral HPLC (Crownpak Cr+ Column 92% ee; $^1$H NMR (DMSO-₆ 250 MHz) δ8.61 (br s, 3H, NH₃), 6.90–7.30 (m, 3H, Ar), 4.53 (br s, 1H), 3.77 (s, 3H, OCH₃), 3.75 (s, 3H, OCH₃), 3.57 (s, 3H, OCH₃), 3.16 (dd, 1H, J₁=6 Hz, J₂=16 Hz), 2.98 (dd, 1H, J₁=8 Hz, J₂=16 Hz); $^{13}$C NMR (DMSO-d₆) δ169.5, 149.0, 148.6, 128.9, 119.8, 111.4, 111.2, 55.6, 55.4, 51.7, 50.7, 38.4. Anal.Calcd for C₁₂H₁₈NO₄Cl 0.48 H₂O. Theoretical C, 50.67; H, 6.72; N, 4.92. Found C, 50.66; H, 6.54; N, 4.81.

EXAMPLE 88

Methyl (3R)-3-amino-3-(3,4-dimethoxyphenyl) propionate (0.25 g, 0.91 mmol), sodium carbonate (0.10 g, 0.91 mmol) and N-carboethoxyphthalimide (0.20 g, 0.91 mmol) were allowed to react according to the procedure of Example 85. Methyl (3R)-3-phthalimido-3-(3,4-dimethoxyphenyl)propionate was obtained as a white powder, 0.29 g (88%); $^1$H NMR (DMSO-₆, 250 MHz) δ7.87 (br s, 4H, Ar), 6.80–7.10 (m, 3H, Ar), 5.64 (dd, 1H, J₁=7 Hz, J₂=9 Hz), 3.73 (s, 3H, OCH₃), 3.72 (s, 3H, OCH₃), 3.55 (s, 3H, OCH₃), 3.30–3.67 (m, 2H); $^{13}$C NMR (DMSO-d₆) δ170.8, 167.6, 148.6, 148.4, 134.7, 131.1, 131.0, 123.2, 119.2, 111.7, 111.0, 55.5, 51.6, 49.9, 35.6. Anal.Calcd for C₂₀H₁₉NO₆0.80 H₂O. Theoretical C, 62.60; H, 4.99; N, 3.69. Found C, 62.60; H, 4.93; N, 3.69. HPLC 99.9%.

EXAMPLE 89

To a stirred solution of methyl 3-amino-3-(3-ethoxy-4-methoxyphenyl)propionate hydrochloride (0.87 g, 3.0 mmol) and sodium carbonate (0.32 g, 3.0 mmol) in a mixture of water (10 mL) and acetonitrile (10 mL) was added N-carbethoxyphthalimide (0.68 g, 3.0 mmol). The resulting solution was stirred for 3 hours at room temperature. The acetonitrile was removed in vacuo. To the resulting mixture was added ether (5 mL) and the mixture was stirred at room temperature overnight allowing the ether to evaporate. The resulting white solid was filtered. The solid was washed with water, air dried, and dried in vacuo (60° C., <1 mm) to afford 1.0 g (87%) of methyl 3-phthalimido-3-(3-ethoxy-4-methoxyphenyl)propionate as a white solid: mp 86°–87° C.; $^1$H NMR (CDCl₃) δ7.86–7.63 (m, 4H), 7.16–7.05 (m, 2H), 6.88–6.76 (m, 1H), 5.77 (dd, J=5.9, 10 Hz, 1H), 4.11 (q, J=7 Hz, 2H), 3.84 (s, 3H), 3.77 (dd, J=10, 6.7 Hz, 1H), 3.63 (s, 3,25 (dd, J=5.9, 165.5 Hz, 1H), 1.45 (t, J=7 Hz, 3H); $^{13}$C NMR (CDCl₃) δ171.0, 168.0, 149.0, 148.2, 133.9, 131.7, 130.9, 123.2, 120.2, 112.5, 111.1, 64.3, 55.8, 51.8, 50.7, 35.8, 14.6; HPLC (Waters Nova-Pak C₁₈ column, 3.9×150 mm, 4 micron, 1 mL/min, 240 nm, 45/55, acetonitrile/0.1% aqueous phosphoric acid 6 min, 100%, Anal. Calcd. for C₂₁H₂₁NO₆. Theoretical: C, 65.79; H, 5.52; N, 3.65. Found: C, 65.71; H, 5.70; N, 3.63.

EXAMPLE 90

To a stirred solution of methyl 3-amino-3-(3-butoxy-4-methoxyphenyl)propionate hydrochloride (0.95 g, 3.0 mmol) and sodium carbonate (0.32 g, 3.0 mmol) in a mixture of water (10 mL) and acetonitrile (10 mL) was added N-carbethoxyphthalimide (0.68 g, 3.0 mmol). The resulting solution was stirred for 3 hours at room temperature. The acetonitrile was removed in vacuo. To the resulting mixture was added ether (5 mL) and the mixture was stirred at room temperature overnight allowing the ether to evaporate. The resulting white solid was filtered. The solid was washed with water, air dried, and dried in vacuo (60° C., <1 mm) to afford 1.1 g (89%) of methyl 3-phthalimido-3-(3-butoxy-4-methoxyphenyl)propionate as a white solid: mp 54°–55° C.; $^1$H NMR (CDCl₃) δ5 7.86–7.63 (m, 4H), 7.16–7.05 (m, 2H), 6.85–6.76 (m, 1H), 5.76 (dd, J=5.9, 10 Hz, 1H), 4.02 (t, J=6.7 Hz, 3.86–3.71 (m, 1H), 3.83 (s, 3H), 3.63 (s, 3H), 3.24 (dd, J=5.9, 16.5 Hz, 1H), 1.89–1.73 (m, 2H), 1.59–1.41 (m, 2H), 1.04–0.89 (m, 3H); $^{13}$C NMR (CDCl₃) δ5 171.1, 168.1, 149.2, 148.5, 133.9, 131.8, 130.9, 123.3, 120.2, 112.7, 111.4, 68.6, 55.9, 51.9, 50.7, 35.9, 31.1, 19.2, 13.9; HPLC (Waters Nova-Pak C₁₈ column, 3.9×150 mm, 4 micron, 1 mL/min, 240 nm, 55/45, acetonitrile/0.1% aqueous phosphoric acid) 6.5 min, 100%, Anal. Calcd. for C₂₃H₂NO₆. Theoretical: C, 67.14; H, 6.12; N, 3.40. Found: C, 66.89; H, 6.15; N, 3.31.

EXAMPLE 91

A solution of 3-phthalimido-3-(3, 4-diisopropoxyphenyl)propionic acid (1.0 g, 2.4 mmol), 1,1 carbonyldiimidazole (0.43 g, 2.6 mmol), and 4-dimethylaminopyridine (trace) in tetrahydrofuran (18 mL) was stirred for 1.5 hours at room temperature. To the solution was added ammonium hydroxide (0.24 mL, 3.7 mmol, 28–30%) and stirring was continued for 2 hours. The tetrahydrofuran was removed in vacuo leaving an oil. To the oil was added 2 mL of water and the mixture was stirred at room temperature overnight. The resulting slurry was filtered, the solid was washed with water, air dried, and dried in vacuo (60° C., <1 mm) to afford 0.87 g (88%) of 3-phthalimido-3-(3, 4-diisopropoxyphenyl) propionamide as a white solid: mp 153°–154.5° C.; $^1$H NMR (DMSO-d₆) δ7.92–7.78 (m, 4H), 7.55 (s, 1H), 7.03(s, 1H), 6.93–6.77 (m, 3H), 5.71–5.56 (m, 1H), 4.51–4.33 (m, 2H), 3.25–3.06 (m, 2H), 1.31–1.08 (m, 12H); $^{13}$C NMR (DMSO-d₆) δ171.7, 168.3, 148.9, 133.9, 132.1, 131.9, 123.3, 120.9, 117.7, 72.2, 72.1, 51.5, 37.9, 22.2; Anal. Calcd. for C₂₃H₂₆N₂O₅. Theoretical: C, 67.30; H, 6.38; N, 6.82. Found: C, 67.01; H, 6.35; N, 6.69.

EXAMPLE 92

A stirred suspension of 3-nitrophthalic anhydride (2.1 g, 10 mmol), sodium acetate (0.82 g, 10 mmol), and methyl 3-amino-3-(3-ethoxy-4-methoxyphenyl) propionate hydrochloride (2.9 g, 10 mmol) in 30 mL of acetic acid was heated to reflux under nitrogen for 12 hours. The acetic acid was removed in vacuo to afford an orange gum which was dissolved in methylene chloride (30 mL) and was washed with a saturated aqueous solution of sodium bicarbonate (35 mL). The organic layer was separated and the aqueous layer was extracted with methylene chloride (30 mL). The combined organic extracts were dried over magnesium sulfate, filtered and concentrated in vacuo to afford 4.0 g (93%) of methyl 3-(3-nitrophthalimido)-3-(3-ethoxy-4-methoxyphenyl) propionate as a yellow solid: mp 56°–57.5° C.; $^1$H NMR (CDCl$_3$) δ8.11–8.04 (m, 2H), 7.94–7.83 (m, 1H), 7.14–7.05 (m, 2H), 6.86–6.76 (m, 1H), 5.76 (dd, J=5.6, 10.3 Hz, 1H), 4.10 (q, J=7 Hz, 2H), 3.84 (s, 3H), 3.91–3.74 (m, 1H), 3.64 (s, 3H), 3.28–3.15 (m, 1H), 1.46 (t, J=7 Hz, 3H); $^{13}$C NMR (CDCl$_3$) δ170.9, 165.6, 162.6, 149.4, 148.3, 145.1, 135.2, 133.8, 130.1, 128.5, 127.0, 123.4, 120.4, 112.6, 111.3, 64.4, 55.9, 51.9, 51.5, 35.4, 14.7; Anal. calcd for $C_{21}H_{20}N_2O_8$. Theoretical: C, 58.88; H, 4.71; N, 6.54. Found: C, 58.89; H, 4.69; N, 6.40.

EXAMPLE 93

To a solution of methyl 3-(3-nitrophthalimido)-3-(3-ethoxy-4-methoxyphenyl)propionate (2.5 g, 5.8 mmol) in 25 mL of ethyl acetate was added 0.25 g of 10% palladium on carbon catalyst. The mixture was hydrogenated in a Parr-Shaker apparatus at 55–60 psi of hydrogen overnight. The reaction mixture was filtered through celite and the filtrate was concentrated in vacuo to afford a yellow solid. The crude product was purified by flash column chromatography (silica gel, 74% ethyl acetate/methylene chloride). The resulting solid was recrystallized (60 mL ethyl acetate/20 mL hexane) and was then dried in vacuo (60° C., <1 mm) to afford 1.28 g (55%) of methyl 3-(3-aminophthalimido)-3-(3-ethoxy-4-methoxyphenyl)propionate as a yellow solid: mp 134°–136° C.; $^1$H NMR (CDCl$_3$) δ7.40–7.26 (m, 1H); 7.16–7.01 (m, 3H), 6.86–6.72 (m, 2H), 5.71 (dd, J=6, 9.8 Hz, 1H), 5.28 (br s, 2H), 4.10 (q, J=7 Hz, 2H), 3.83 (s, 3H), 3.73 (dd, J=9.8, 16.5 Hz, 1H), 3.64 (s, 3H), 3.24 (dd, J=6, 16.5 Hz, 1H), 1.44 (t, J=7 Hz, 3H); $^{13}$C NMR (CDCl$_3$) δ171.1, 169.8, 168.3, 148.9, 148.1, 145.3, 134.9, 132.3, 131.3, 120.9, 120.0, 112.5, 112.4, 111.1, 110.8, 64.2, 55.8, 51.8, 50.2, 36.0, 14.6; HPLC (Waters Nova-Pak C$_{18}$ column, 3.9×150 mm, 4 micron, 1 mL/min, 240 nm, 50/50, acetonitrile/0.1% aqueous phosphoric acid) 5 min, 100%; Anal. Calcd. for $C_{21}H_{22}N_2O_6$. Theoretical: C, 63.31,H, 5.57, N, 7.03. Found: C, 63.11; H, 5.50; N, 6.99.

EXAMPLE 94

A stirred suspension of 4-nitrophthalic anhydride (1.6 g, 7.0 mmol), sodium acetate (0.6 g, 7 mmol), and methyl 3-amino-3-(3-ethoxy-4-methoxyphenyl) propionate hydrochloride (2 g, 7 mmol) in 25 mL of acetic acid was heated to reflux under nitrogen for 3.5 hours. The acetic acid was removed in vacuo to afford an orange gum which was dissolved in methylene chloride (20 mL) and was washed with a saturated aqueous solution of sodium bicarbonate (10 mL). The organic layer was separated and the aqueous layer was extracted with methylene chloride (10 mL). The combined organic extracts were dried over magnesium sulfate, filtered and concentrated in vacuo to afford 2.8 g (93%) of methyl 3-(4-nitrophthalimido)-3-(3-ethoxy-4-methoxyphenyl) propionate as a yellow solid: mp 54°–61° C.; $^1$H NMR (CDCl$_3$) δ8.66–8.52 (m, 2H), 8.05–7.96 (m, 1H), 7.16–7.06 (m, 2H), 6.89–6.77 (m, 1H), 5.76 (dd, 1=5.4, 10.5 Hz, 1H), 4.10 (q, J=7 Hz, 2H), 3.86 (s, 3H), 3.85 (dd, J=10.5, 16.8 Hz, 1H), 3.20 (dd, J=16.8, 5.4 Hz, 1H), 1.46 (t, J=7 Hz, 3H); $^{13}$C NMR (CDCl$_3$) δ170.9, 165.9, 165.7, 151.7, 149.4, 148.4, 136.2, 133.2, 130.2, 129.2, 124.5, 120.3, 118.7, 112.4, 111.3, 64.4, 55.9, 52.0, 51.5, 35.5, 14.7; Anal. calcd for $C_{21}H_{20}N_2O_8$. Theoretical: C, 58.88; H, 4.71; N, 6.54. Found: C, 58.92; H, 4.59; N, 6.48.

EXAMPLE 95

To a solution of methyl 3-(4-nitrophthalimido)-3-(3-ethoxy-4-methoxyphenyl)propionate (2.3 g, 5.4 mmol) in 25 mL of ethyl acetate was added 0.25 g of 10% palladium on carbon catalyst. The mixture was hydrogenated in a Parr-Shaker apparatus at 55–60 psi of hydrogen overnight. The reaction mixture was filtered through celite and the filtrate was concentrated in vacuo to afford a yellow solid. The crude product was purified by flash column chromatography (silica gel, 20% ethyl acetate/methylene chloride). The resulting solid was dried in vacuo (60° C., <1 mm) to afford 1.98 g (93%) of methyl 3-(4-aminophthalimido)-3-(3-ethoxy-4-methoxyphenyl)propionate as a yellow solid: mp 65°–67° C.; $^1$H NMR (CDCl$_3$) δ7.56–7.48 (m, 1H); 7.15–6.93 (m, 3H), 6.85–6.71 (m, 2H), 5.70 (dd, J=6.1, 9.7 Hz, 1H), 4.35 (br s, 2H), 4.09 (q, J=7 Hz, 2H), 3.83 (s, 3H), 3.72 (dd, J=9.7, 16.4 Hz, 1H), 3.62 (s, 3H), 3.23 (dd, J=6.1, 16.4 Hz, 1H), 1.44 (t, J=7 Hz, 3H); $^{13}$C NMR (CDCl$_3$) δ171.2, 168.3, 168.2, 152.3, 148.9, 148.1, 134.6, 131.4, 125.1, 120.3, 120.2, 117.9, 112.6, 111.2, 108.4, 64.3, 55.9, 51.8, 50.4, 38.1, 14.7; HPLC (Waters Radial-Pak Phenyl column, 1.8×100 mm, 1 mL/min, 240 nm, 55/45, acetonitrile/0.1% aqueous phosphoric acid) 3.5 min, 100%; Anal. Calcd. for $C_{21}H_{22}N_2O_6 \cdot 0.29\ H_2O$. Theoretical: C, 62.49,H, 5.63, N, 6.94. Found: C, 62.53; H, 5.62; N, 6.78.

EXAMPLE 96

A stirred suspension of 3-nitrophthalic anhydride (0.24 g, 1.13 mmol) and 3-amino-3-(3-ethoxy-4-methoxyphenyl) propanenitrile (0.25 g, 1.13 mmol) in 6 mL of acetic acid was heated to reflux under nitrogen for 12 hours. The acetic acid was removed in vacuo to afford an orange gum which was dissolved in methylene chloride (10 mL) and was washed with a saturated aqueous solution of sodium bicarbonate (2×10 mL). The organic layer was separated and the aqueous layer was extracted with methylene chloride (10 mL). The combined organic extracts were dried over magnesium sulfate, filtered and concentrated in vacuo to afford a yellow oil. The crude product was purified by flash column chromatography (silica gel, 5% ethyl acetate/methylene chloride) and the resulting solid was dried in vacuo (60° C., <1 mm) to afford 0.25 g (56%) of 3-(3-nitrophthalimido)-3-(3-ethoxy-4-methoxyphenyl)propanenitrile as a yellow solid: mp 155.5°–157° C.; $^1$H NMR (CDCl$_3$) δ8.20–8.09 (m, 2H), 8.02–7.86 (m, 1H), 7.15–7.02 (m, 2H), 6.88–6.76 (m, 1H), 5.64 (dd, J=6.3, 10.6 Hz, 1H), 4.09 (q, J=7 Hz, 2H), 3.85 (s, 3H), 3.84 (dd, J=10.6, 16.7 Hz, 1H), 3.26 (dd, J=6.3, 16.7 Hz, 1H), 1.46 (t, J=7 Hz, 3H); $^{13}$C NMR (CDCl3) δ165.3, 162.3, 150.1,148.7, 144.9, 135.7, 133.5, 129.0, 128.1,127.4, 123.2, 120.3, 116.6, 112.1, 111.5, 64.6, 55.9, 51.9, 20.9, 14.7; Anal. calcd for $C_{20}H_{17}N_3O_6$. Theoretical: C, 60.76; H, 4.33; N, 10.63. Found: C, 60.59; H, 4.22; N, 10.65.

EXAMPLE 97

To a solution of 3-(3-nitrophthalimido)-3-(3-ethoxy-4-methoxyphenyl)propanenitrile (0.2 g, 0.5 mmol) in 30 mL of ethyl acetate was added 0.05 g of 10% palladium on carbon catalyst. The mixture was hydrogenated in a Parr-Shaker apparatus at 55–60 psi of hydrogen overnight. The reaction mixture was filtered through celite and the filtrate was concentrated in vacuo to afford a yellow oil. The crude product was purified by flash column chromatography (silica gel, 3% ethyl acetate/methylene chloride). The resulting yellow solid was then dried in vacuo (60° C., <1 mm) to afford 0.09 g (50%) of 3-(3-aminophthalimido)-3-(3-ethoxy-4-methoxyphenyl)propanenitrile: mp 171°–172.5° C.; $^1$H NMR (CDCl$_3$) δ7.47–7.356 (m, 1H); 7.19–7.00 (m, 3H), 6.90–6.29 (m, 2H), 5.56 (dd, J=6.6 10 Hz, 1H), 5.24 (s, 2H), 4.09 (q, J=7 Hz, 2H), 3.84 (s, 3H) 3.77 (dd, J=10, 16.8 Hz, 1H), 3.27 (dd, J=6.6, 16.8 Hz, 1H), 1.45 (t, J=7 Hz, 3H); $^{13}$C NMR (CDCl$_3$) δ169.4, 167.9, 149.6, 148.5, 145.5, 135.5, 132.1, 129.4, 121.3, 120.0, 117.1, 113.0, 112.2, 111.4, 110.6, 64.5, 55.9, 50.7, 21.1, 14.7; HPLC (Waters Nova-Pak C$_{18}$ column, 3.9×150 mm, 4 micron, 1 mL/min, 240 nm, 40/60, acetonitrile/0.1% aqueous phosphoric acid) 4.5 min, 100%; Anal. Calcd. for C$_{20}$H$_{19}$N$_3$O$_4$. Theoretical: C, 65.74; H, 5.24, N, 11.50. Found: C, 65.54; H, 5.23; N, 11.23.

EXAMPLE 98

To a solution of methyl 3-(4-nitrophthalimido)-3-(3, 4-diethoxyphenyl)propionate (1.87 g, 4.23 mmol) in a mixture of ethyl acetate (30 mL) and methanol (30 mL) was added 0.18 g of 10% palladium on carbon catalyst. The mixture was hydrogenated in a Parr Shaker apparatus at 55–60 psi of hydrogen overnight. The reaction mixture was filtered through celite and the filtrate was concentrated in vacuo to afford 1.67 g of a yellow solid. The crude product was purified by flash column chromatography (silica gel, 35% ethyl acetate/hexane). The resulting solid was then dried in vacuo (60° C., <1 mm) to afford 1.1 g (63%) of methyl 3-(4-aminophthalimido)-3-(3, 4-diethoxyphenyl) propionate as a yellow solid: mp 143°–145° C.; $^1$H NMR (CDCl$_3$) δ7.53–7.44 (m, 1H); 6.99–6.78 (m, 5H), 6.52 (s, 2H), 5.54 (dd, J=6.4, 9.5 Hz, 1H), 4.05–3.89 (m, 4H), 3.66–3.48 (m, 1H), 3.55 (s, 3H), 3.35–3.20 (m, 1H), 1.37.1.2 (m, 6H); $^{13}$C NMR (CDCl$_3$) δ170.9, 168.1, 167.7, 155.1, 147.9, 147.8, 134.1, 131.6, 125.1, 119.3, 116.8, 116.1, 113.2, 112.6, 106.9, 63.8, 63.8, 51.5, 49.5, 14.7, 14.7; Anal. Calcd. for C$_{22}$H$_{24}$N$_2$O$_6$. Theoretical: C, 64.07,H, 5.87, N, 6.79. Found: C, 63.97; H, 5.73; N, 6.97.

EXAMPLE 99

A stirred mixture of phthalic dicarboxaldehyde (2.68 g, 20.0 mmol) and 3-amino-3-(3-ethoxy-4-methoxyphenyl) propionic acid (4.78 g, 20.0 mmol) in glacial acetic acid (50 mL) under nitrogen was heated to reflux for 5 minutes. The reaction mixture was then allowed to cool to room temperature and was concentrated in vacuo to afford a yellow solid. The crude product was recrystallized twice from refluxing ethanol (150 mL). The resulting solid was then dried in vacuo (60° C., <1 mm) to afford 4.4 g (62%) of 3-(1-oxoisoindolin-2-yl)-3-(3-ethoxy-4-methoxyphenyl) propionic acid as a white solid: mp 193.5°–194° C.; $^1$H NMR (DMSO-d$_6$) δ12.40 (br s, 1H), 7.75–7.40 (m, 4H), 7.05–6.85 (m, 3H), 5.71 (m, 1H), 4.51 (d, J=17.7 Hz, 1H), 4.11 (d, J=17.7 Hz, 1H), 3.99 (m, 2H), 3.73 (s, 3H), 3.25–3.02 (m, 2H), 1.30 (t, J=6.9 Hz, 3H), $^{13}$C NMR (DMSO-d$_6$) δ171.9, 166.9, 148.5, 147.9, 141.7, 132.2, 131.6, 131.4, 127.9, 123.5, 122.9, 119.3, 111.8, 63.7, 55.4, 51.2, 46.3, 36.8, 14.7; Anal. Calcd. for C$_{20}$H$_{21}$NO$_5$. Theoretical: C, 67.59; H, 5.96; N, 3.94. Found: C, 67.64; H, 5.97; N, 3.92.

EXAMPLE 100

A mixture of 3-(1-oxoisoindolin-2-yl)-3-(3-ethoxy-4-methoxyphenyl)propionic acid (12.6 g, 35.4 mmol) and 1,1'-carbonyldiimidazole (5.97 g, 36.8 mmol), in tetrahydrofuran (100 mL) was stirred for 1.5 hours at room temperature. To the solution was added ammonium hydroxide (7.5 mL, 112.5 mmol, 28–30%) and stirring was continued for 20 minutes. The tetrahydrofuran was removed in vacuo and the remaining residue was slurried in 100 mL of water for 30 minutes. The mixture was filtered and the white solid was washed with water (150 mL), air dried and dried in vacuo (60° C., <1 mm). The resulting solid was recrystallized form ethyl acetate (1.1 L) and was then dried in vacuo (60° C., <1 mm) to afford 9.61 g (77%) of 3-(1-oxoisoindolin2-yl)-3-(3-ethoxy-4-methoxyphenyl) propionamide as a white solid: mp 169–171.5; $^1$H NMR (DMSO-d$_6$) δ7.75–7.40 (m, 5H), 7.05–6.80 (m, 4H), 5.75 (m, 1H), 4.56 (d, J=17.6 Hz, 1H), 4.14 (d, J=17.6 Hz, 1H), 3.98 (m, 2H), 3.72 (s, 3H), 2.93 (m, 2H), 1.30 (t, J=6.9 Hz, 3H), $^{13}$C NMR (DMSO-d$_6$) δ171.2, 166.8, 148.3, 147.8, 141.6, 132.2, 132.1, 131.2, 127.8, 123.4, 122.7, 119.1, 112.1, 111.7, 63.6, 55.4, 51.3, 46.2, 37.8, 14.6; Anal. Calcd. for C$_{20}$H$_{22}$N$_2$O$_5$. Theoretical: C, 67.78; H, 6.26; N, 7.90. Found: C, 67.89; H, 6.31; N, 7.83.

EXAMPLE 101

To an ice bath cooled solution of 50 mL of methanol was added acetyl chloride (7.2 mL, 100 mmol). After stirring for 10 minutes 3-(1-oxoisoindolin-2-yl)-3-(3-ethoxy-4-methoxyphenyl)propionic acid (6.00 g, 16.9 mmol) was added to the mixture. After 30 minutes the ice bath was removed and the reaction was monitored by HPLC (Waters radial pak phenyl 8×100 mm column, 240 mn, 1.5 mL/min, 35/65 acetonitrile/0.1% phosphoric acid). After 4 hours the reaction had reached completion. The methanol was removed in vacuo and the resulting residue was diluted with 50 mL of methylene chloride. The mixture was extracted with aqueous sodium bicarbonate (50 mL) and brine. The organic layer was dried over sodium sulfate, filtered and concentrated in vacuo to afford a thick oil. Hexane (50 mL) and ether (5 mL) were added to the oil and the mixture stirred overnight in an open flask. An additional 25 mL of hexane were added to facilitate stirring. After 6 hours the slurry was filtered and the solid air dried and then dried in vacuo (60° C., <1 mm) to afford 5.45 g (87%) of methyl 3-(1-oxoisoindolin-2-yl)-3-(3-ethoxy-4-methoxyphenyl) propionate as a white solid: mp 78°–80° C.; $^1$H NMR (DMSO-d$_6$) δ7.75–7.40 (m, 4H), 7.10–6.80 (m, 3H), 5.72 (t, J=7.8 Hz, 1H), 4.51 (d, J=17.7 Hz, 1H), 4.09 (d, J=17.7 Hz, 1H), 3.97 (m, 2H), 3.73 (s, 3H), 3.55 (s, 3H), 3.24 (m, 2H), 1.30 (m, 3H); $^{13}$C NMR (DMSO-d$_6$) δ170.8, 166.8, 148.5, 147.9, 141.6, 132.0, 131.3, 131.2, 127.8, 123.4, 122.8, 119.3, 112.2, 111.8, 63.7, 55.4, 51.5, 51.0, 46.3, 36.2, 14.6; Anal. Calcd. for C$_{21}$H$_{23}$NO$_5$. Theoretical: C, 68.28; H, 6.28; N, 3.79. Found: C, 68.13; H, 6.27; N, 3.70.

EXAMPLE 102

Tablets, each containing 50 mg of 3-phenyl-2-(1-oxoisoindolin-2-yl)propionic acid, can be prepared in the following manner:

| Constituents (for 1000 tablets) | |
|---|---|
| 3-phenyl-2-(1-oxo isoindolin-2-yl)propionic acid | 50.0 g |
| lactose | 50.7 g |
| wheat starch | 7.5 g |
| polyethylene glycol 6000 | 5.0 g |
| talc | 5.0 g |

-continued

| Constituents (for 1000 tablets) | |
|---|---|
| magnesium stearate | 1.8 g |
| demineralized water | q.s. |

The solid ingredients are first forced through a sieve of 0.6 mm mesh width. The active ingredient, the lactose, the talc, the magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 103

Tablets, each containing 100 mg of 3-phenyl-3-(1-oxoisoindolin-2-yl)propionamide as active ingredient, can be prepared in the following manner:

| Constituents (for 1000 tablets) | |
|---|---|
| 3-phenyl-3-(1-oxoiso indolin-2-yl)propionamide | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, the lactose, the magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 104

Tablets for chewing, each containing 75 mg of 3-(4-methoxyphenyl)-3-(1-oxoisoindolin-2-yl)propionamide as active ingredient, can be prepared in the following manner:

| Composition (for 1000 tablets) | |
|---|---|
| 3-(4-methoxyphenyl)-3-(1-oxo-isoindolin-2-yl)propionamide | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 105

Tablets, each containing 10 mg of 3-(3,4-dimethoxyphenyl)-3-(1-oxoisoindolin-2-yl)propionic acid as active ingredient, can be prepared in the following manner:

| Composition (for 1000 tablets) | |
|---|---|
| 3-(3,4-dimethoxyphenyl)-3-(1-oxoisoindolin-2-yl) propionic acid | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active ingredient, lactose, talc, magnesium stearate and half of the starch are intimately mixed. The other half the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 106

Gelatin dry-filled capsules, each containing 100 mg of 3-(3,4-dimethoxyphenyl)-3-(1-oxoisoindolin-2-yl) propionamide as active ingredient, can be prepared in the following manner:

| Composition (for 1000 capsules) | |
|---|---|
| 3-(3,4-dimethoxyphenyl)-3-(1-oxo-isoindolin-2-yl)-propionamide | 100.0 g |
| microcrystalline cellulose | 30.0 g |
| sodium lauryl sulphate | 2.0 g |
| magnesium stearate | 8.0 g |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 107

A 0.2% injection or infusion solution can be prepared, for example, in the following manner:

| | |
|---|---|
| 3-(1-oxoisoindolin-2-yl)-3-(3-ethoxy-4-methoxyphenyl)-propionic acid sodium salt | 5.0 g |
| sodium chloride | 22.5 g |
| phosphate buffer pH 7.4 | 300.0 g |
| demineralized water q.s. | 2500.0 mL |

The active ingredient is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of active ingredient).

What is claimed is:

1. A compound of the formula:

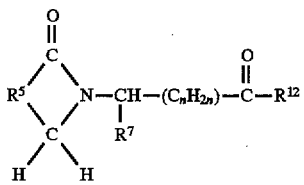

in which:

n has a value of 1, 2, or 3;

$R^5$ is o-phenylene, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, alkoxy of 1 to 10 carbon atoms, and halo;

$R^7$ is (i) phenyl or phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (ii) benzyl unsubstituted or substituted with 1 to 3 substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (iii) naphthyl, and (iv) benzyloxy;

$R^{12}$ is —OH, alkoxy of 1 to 12 carbon atoms, or

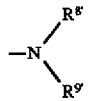

$R^{8'}$ is hydrogen or alkyl of 1 to 10 carbon atoms; and $R^{9'}$ is hydrogen, alkyl of 1 to 10 carbon atoms, —COR$^{10}$, or —SO$_2$R$^{10}$ in which $R^{10}$ is hydrogen, alkyl of 1 to 10 carbon atoms, or phenyl.

2. A compound according to claim 1 in which $R^{12}$ is

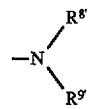

$R^{8'}$ and $R^{9'}$ are as therein defined.

3. A compound according to claim 2 in which $R^5$ is o-phenylene, unsubstituted or substituted with 1 to 4 substituents each selected independently of the other from the group consisting of amino, alkyl of 1 to 4 carbon atoms, alkoxy of 1 to 4 carbon atoms, and halo, $R^7$ is phenyl monosubstituted or disubstituted with nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, n is 1, and each of $R^{8'}$ and $R^{9'}$ is hydrogen.

4. A compound according to claim 3 in which $R^7$ is phenyl substituted with 1 to 3 alkoxy groups of 1 to 4 carbon atoms.

5. A compound according to claim 4 wherein $R^7$ is phenyl substituted with alkoxy of 1 to 4 carbon atoms in the 3- and 4-positions.

6. A compound according to claim 1 in which $R^{12}$ is —OH.

7. A compound according to claim 6 in which $R^5$ is o-phenylene, unsubstituted or substituted with 1 to 4 substituents each selected independently of the other from the group consisting of amino, alkyl of 1 to 4 carbon atoms, alkoxy of 1 to 4 carbon atoms, and halo, $R^7$ is phenyl monosubstituted or disubstituted with nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, and n is 1.

8. A compound according to claim 7 in which $R^7$ is phenyl substituted with 1 to 3 alkoxy groups of 1 to 4 carbon atoms.

9. A compound according to claim 8 wherein $R^7$ is phenyl substituted with alkoxy of 1 to 4 carbon atoms in the 3- and 4-positions.

10. A compound according to claim 1 in which $R^{12}$ is alkoxy of 1 to 12 carbon atoms.

11. A compound according to claim 10 in which $R^5$ is o-phenylene, unsubstituted or substituted with 1 to 4 substituents each selected independently of the other from the group consisting of amino, alkyl of 1 to 4 carbon atoms, alkoxy of 1 to 4 carbon atoms, and halo, $R^7$ is phenyl monosubstituted or disubstituted with nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, n is 1, and $R^{12}$ is alkoxy of 1 to 6 carbon atoms.

12. A compound according to claim 11 in which $R^7$ is phenyl substituted with 1 to 3 alkoxy groups of 1 to 4 carbon atoms.

13. A compound according to claim 12 wherein $R^7$ is phenyl substituted with alkoxy of 1 to 4 carbon atoms in the 3- and 4-positions.

14. A compound according to claim 1 which is 3-phenyl-2-(1-oxoisoindolin-2-yl)propionic acid.

15. A compound according to claim 1 which is 3-phenyl-2-(1-oxoisoindolin-2-yl)propionamide.

16. A compound according to claim 1 which is 3-phenyl-3-(1-oxoisoindolin-2-yl)propionic acid.

17. A compound according to claim 1 which is 3-phenyl-3-(1-oxoisoindolin-2-yl)propionamide.

18. A compound according to claim 1 which is 3-(4-methoxyphenyl)-3-(1-oxoisoindolin-yl)propionic acid.

19. A compound according to claim 1 which is 3-(4-methoxyphenyl)-3-(1-oxoisoindolin-yl)propionamide.

20. A compound according to claim 1 which is 3-(3,4-dimethoxyphenyl)-3-(1-oxoisoindolin-2-yl)propionic acid.

21. A compound according to claim 1 which is 3-(3,4-dimethoxyphenyl)-3-(1-oxoisoindolin-2-yl)propionamide.

22. A compound according to claim 1 which is 3-(3,4-diethoxyphenyl)-3-(1-oxoisoindolin-yl)propionic acid.

23. A compound according to claim 1 which is methyl 3-(1-oxoisoindolin-2-yl)-3-(3-ethoxy-4-methoxyphenyl) propionate.

24. A compound according to claim 1 which is 3-(1-oxoisoindolin-2-yl)-3-(3-ethoxy-4-methoxyphenyl) propionic acid.

25. A compound according to claim 1 which is 3-(1-oxoisoindolin-2-yl)-3-(3-propoxy-4-methoxyphenyl) propionic acid.

26. A compound according to claim 1 which is 3-(1-oxoisoindolin-2-yl)-3-(3-butoxy-4-methoxyphenyl) propionic acid.

27. A compound according to claim 1 which is 3-(1-oxoisoindolin-2-yl)-3-(3-propoxy-4-methoxyphenyl) propionamide.

28. A compound according to claim 1 which is 3-(1-oxoisoindolin-2-yl)-3-(3-butoxy-4-methoxyphenyl) propionamide.

29. A compound according to claim 1 which is methyl 3-(1-oxoisoindolin-2-yl)-3-(3-butoxy-4-methoxyphenyl) propionate.

30. A compound according to claim 1 which is methyl 3-(1-oxoisoindolin-2-yl)-3-(3-propoxy-4-methoxyphenyl) propionate.

31. The method of reducing levels of TNFα in a mammal which comprises administering thereto an effective amount of a compound according to claim 1.

32. A pharmaceutical composition comprising a quantity of a compound according to claim 1 sufficient upon administration in a single or multiple dose regimen to reduce levels of TNFα in a mammal in combination with a carrier.

33. A compound of the formula:

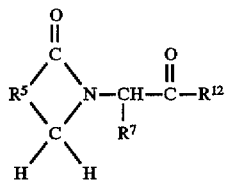

in which:

$R^5$ is o-phenylene, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, alkoxy of 1 to 10 carbon atoms, and halo;

$R^7$ is (i) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo; (ii) benzyl unsubstituted or substituted with 1 to 3 substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo; (iii) naphthyl; and (iv) benzyloxy;

$R^{12}$ is —OH, alkoxy of 1 to 12 carbon atoms, or

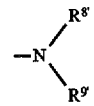

$R^{8'}$ is hydrogen or alkyl of 1 to 10 carbon atoms; and $R^{9'}$ is hydrogen, alkyl of 1 to 10 carbon atoms, —$COR^{10}$, or —$SO_2R^{10}$ in which $R^{10}$ is hydrogen, alkyl of 1 to 10 carbon atoms, or phenyl.

34. A compound according to claim 33 in which $R^5$ is o-phenylene, unsubstituted or substituted with 1 to 4 amino, alkyl of 1 to 4 carbon atoms, alkoxy of 1 to 4 carbon atoms, or halo substituents, $R^7$ is phenyl monosubstituted or disubstituted with nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, $R^{12}$ is

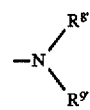

in which each of $R^{8'}$ and $R^{9'}$ is hydrogen.

35. A compound according to claim 34 which is a α-(1-oxoisoindolin-2-yl)phenylacetamide.

* * * * *